United States Patent
Ferguson

(10) Patent No.: US 10,730,871 B2
(45) Date of Patent: Aug. 4, 2020

(54) IMMUNOMODULATORS AND IMMUNOMODULATOR CONJUGATES

(71) Applicant: REGENTS OF THE UNIVERSITY OF MINNESOTA, Minneapolis, MN (US)

(72) Inventor: David Ferguson, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 44 days.

(21) Appl. No.: 15/418,561

(22) Filed: Jan. 27, 2017

(65) Prior Publication Data

US 2017/0217960 A1 Aug. 3, 2017

Related U.S. Application Data

(60) Provisional application No. 62/288,245, filed on Jan. 28, 2016, provisional application No. 62/288,268, filed on Jan. 28, 2016, provisional application No. 62/288,252, filed on Jan. 28, 2016.

(51) Int. Cl.
| C07D 471/04 | (2006.01) |
| A61K 39/36 | (2006.01) |
| A61K 39/39 | (2006.01) |

(52) U.S. Cl.
CPC ............ *C07D 471/04* (2013.01); *A61K 39/39* (2013.01)

(58) Field of Classification Search
CPC ... C07D 471/04; A61K 39/39; A61K 31/4345
USPC ............................................ 546/79; 514/290
See application file for complete search history.

(56) References Cited

U.S. PATENT DOCUMENTS

| 6,696,076 B2 | 2/2004 | Tomai et al. | |
| 7,091,214 B2 | 8/2006 | Hays et al. | |
| 8,658,666 B2* | 2/2014 | Rice | C07D 401/04 514/290 |
| 8,728,486 B2 | 5/2014 | David et al. | |
| 9,034,226 B2* | 5/2015 | Betz | B29C 45/376 264/328.1 |
| 9,034,336 B2* | 5/2015 | Ferguson | A61K 47/62 424/184.1 |
| 9,441,005 B2 | 9/2016 | David et al. | |
| 9,884,866 B2 | 2/2018 | Ferguson et al. | |
| 2006/0188913 A1 | 8/2006 | Krieg et al. | |
| 2007/0213356 A1 | 9/2007 | Merrill et al. | |
| 2008/0213308 A1 | 9/2008 | Valiante et al. | |
| 2014/0212442 A1* | 7/2014 | Ferguson | C07D 471/04 424/184.1 |
| 2016/0068533 A1 | 3/2016 | Ferguson et al. | |
| 2018/0134701 A1 | 5/2018 | David et al. | |

FOREIGN PATENT DOCUMENTS

| EP | 1487485 B1 | 12/2010 | |
| WO | 2003094836 A2 | 11/2003 | |
| WO | 2006031878 A2 | 3/2006 | |
| WO | 2006091394 A2 | 8/2006 | |
| WO | 2007109810 A2 | 9/2007 | |
| WO | 2007109813 A1 | 9/2007 | |
| WO | 2013033345 A1 | 3/2013 | |
| WO | WO-2013033345 A1 * | 3/2013 | ........... C07D 471/04 |

OTHER PUBLICATIONS

Peter Cariuk et al Correlations of PDE-4 Inhibition between Enzymes of Smooth Muscle and Inflammatory Cell source (Year: 1998).*
Discover of Imidazoquinolines with Toll-Like Receptor 7/8 independent Cytokine Induction , Ce Shi et al , (Year: 2012).*
Federal registry, vol. 75. No. 169. (Year: 2010).*
Gowhar Ali et al . Input of Isosteric and Bioisosteric approach to Drug design (Year: 2013).*
Ce Shi et al Discovery of Imidazoquinolines with toll-like receptors 7/8 Independent cytokine induction. (Year: 2012).*
Coffman, et al., "Vaccine adjuvants: putting innate immunity to work", Immunity 33, 492-503 (2010).
Dockrell, et al., "Imiquimod and resiquimod as novel immunomodulators", Journal of Antimicrobial Chemotherapy 48, 751-755 (2001).
Edwards, et al., "Toll-like receptor expression in murine DC subsets: lack of TLR7 expression by CD8 alpha+ DC correlates with unresponsiveness to imidazoquinolines", Eur J Immunol 33 (4), 827-833 (2003).
Ferguson, "Selective Activation of Toll-like Receptor 7 and 8 in the Design of Cancer Vaccines, Discovery on Target, Immunomodulatory Small Molecules", 15th Annual Discovery on Target, Boston, MA, Sep. 25, 2017.
Gibson, et al., "Plasmacytoid dendritic cells produce cytokines and mature in response to the TLR7 agonists, miquimod and resiquimod", Cell Immunol. 218 (1-2), 74-86 (2002).
Gill, et al., "Use of imiquimod 5% cream (Aldara) in cats with multicentric squamous cell carcinoma in situ: 12 cases (2002-2005)", Vet Comp Oncol., 6 (1), 55-64 (2008).
Ingale, et al., "Robust immune responses elicited by a fully synthetic three-component vaccine", Nat Chem Biol. 3 (10), 663-667 (2007).

(Continued)

*Primary Examiner* — Rita J Desai
(74) *Attorney, Agent, or Firm* — Viksnins Harris Padys Malen LLP

(57) ABSTRACT

The invention provides compounds of formula I:

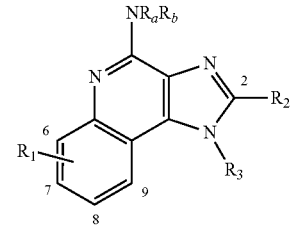

wherein $R_1$-$R_3$, $R^a$, and $R^b$ have any of the values defined herein, and salts thereof. The compounds have immunomodulatory properties.

12 Claims, No Drawings

(56) References Cited

OTHER PUBLICATIONS

Kastenmuller, et al., "Protective T cell immunity in mice following protein-TLR7/8 agonist-conjugate immunization requires aggregation, type I IFN, and multiple DC subsets", J Clin Invest 121 (5), 1782-1796 (2011).

Krishnamachari, et al., "Innovative strategies for co-delivering antigens and CpG oligonucleotides", Adv Drug Delivery Rev. 61 (3), 205-217 (2009).

Larson, et al., "Design and Synthesis of N1-Modified Imidazoquinoline Agonists for Selective Activation of Toll-like Receptors 7 and 8", ACS Med Chem Lett, DOI: 10.1021/acsmedchemlett.7b00256, published on Web Oct. 16, 2017.

Lu, et al., "Treatment failure of a TLR-7 agonist occurs due to self-regulation of acute inflammation and can be overcome by IL-10 blockade", J Immunol 184, 5360-5367 (2010).

Nierkens, et al., "In vivo colocalization of antigen and CpG [corrected] within dendritic cells is associated with the efficacy of cancer immunotherapy", Cancer Res. 68 (13), 5390-5396 (2008).

Philbin, et al., "Immunostimulatory Activity of Toll-Like Receptor 8 Agonists Towards Human Leucocytes: Basic Mechanisms and Translational Opportunities", Biochem Soc Trans 35 (Pt 6), 1485-1491 (2007).

Schiaffo, et al., "Structure-activity relationship analysis of imidazoquinolines with Toll-like receptors 7 and 8 selectivity and enhanced cytokine induction", J Med Chem 57 (2), 339-347 (2014).

Shi, et al., "Discovery of Imidazoquinolines with Toll-Like Receptor 7/8 Independent Cytokine Induction", ACS Med. Chem. Lett. 3, 501-504 (2012).

Shukla, et al., "Structure—Activity Relationships in Human Toll-Like Receptor 7-Active Imidazoquinoline Analogues", J. Med. Chem. 53, 4450-4465 (2010).

WU, et al., "Resiquimod: a new immune response modifier with potential as a vaccine adjuvant for Th1 immune responses", Antiviral Res 64, 79-83 (2004).

\* cited by examiner

IMMUNOMODULATORS AND IMMUNOMODULATOR CONJUGATES

PRIORITY

This application claims priority to U.S. Provisional Patent Application No. 62/288,245, filed 28 Jan. 2016, and to U.S. Provisional Patent Application No. 62/288,268, filed 28 Jan. 2016, and to U.S. Provisional Patent Application No. 62/288,252, filed 28 Jan. 2016. The entire content of U.S. Provisional Patent Application No. 62/288,245 U.S. Provisional Patent Application No. 62/288,268, and U.S. Provisional Patent Application No. 62/288,252 is hereby incorporated herein by reference.

BACKGROUND OF THE INVENTION

Vaccines contain two components: antigen and adjuvant. The antigen is the molecular structure encoded by the pathogen or tumor against which the immune response is directed. To activate an antigen-specific immune response, the antigen must be presented in the appropriate immunostimulatory microenvironment. Adjuvants establish such microenvironments by stimulating the production of immune-activating molecules such as proinflammatory cytokines. Vaccine efficacy depends on the types of antigen and adjuvant, and how they are administered. Striking the right balance among these components is key to eliciting protective immunity.

Toll-like receptors (TLR) sense infection by recognizing pathogen associated molecular patterns and triggering inflammation. Therefore TLR ligands have been developed as vaccine adjuvants. The uptake of antigen and activation of TLR signaling by adjuvants are dynamic, extremely tenuous processes. Ideally, antigen-presenting cells (APC) that engulf antigen will also take up TLR ligand, resulting in upregulation of co-stimulatory molecules, secretion of inflammatory cytokines, and presentation of antigen to T cells. This is certainly the case when APCs process viral particles, which contain both TLR ligands (e.g., dsRNA) and viral proteins. However, in the case of cancer vaccines the antigen and TLR ligand have been administered in mixture. This approach can result in several theoretical outcomes at the injection site: APCs that engulf antigen alone, TLR ligand alone, or TLR ligand with antigen (the desired outcome). Thus, co-administration can create a problem of signal to noise in the resulting immune response. Even when antigen and TLR ligand are engulfed by the same APC, the timing is critical. This was best demonstrated by Nierkens et al, who showed that uptake of TLR9 ligand prior to antigen significantly reduced cross presentation of antigen to CTLs relative to concurrent uptake (Nierkens S, et al., *Cancer Res.* 2008;68:5390-5396). Accordingly, Ingale et al. have demonstrated that direct conjugation of TLR2 ligands to antigen by a covalent bond increased the titer of tumor-reactive IgG over 100,000 times relative to vaccination with a mixture of each component (Ingale S, et al., *Nat Chem Biol.* 2007;3: 663-667). Similarly, coupling antigen to TLR9 ligands increases the number of antigen-specific T cells 5 to 100 fold relative to co-administration of the two components separately (Krishnamachari Y, Salem AK. *Adv Drug Deliv Rev.* 2009; 61:205-217).

Imidazoquinoline is a double cyclic organic molecule that has been exploited as a vaccine adjuvant. Imiquimod is an FDA-approved immune response modifier administered as a cream on the skin for the treatment of cutaneous tumors. Imiquimod exerts its immunostimulatory effects through TLR 7 expressed on plasmacytoid dendritic cells and B cells in humans. Imiquimod treatment causes release of proinflammatory cytokines including interferonα, interferonγ, and IL-12, all of which are important for priming a robust $T_h1$ immune response associated with anti-tumor and anti-viral activity in animals. Topical imiquimod has been used as a vaccine adjuvant with modest success in numerous studies targeting established tumors and viral infection. However the efficacy of imiquimod is restrained by relying solely on TLR7 signaling because TLR7 is not expressed in one of the most abundant professional APCs, the CD8α⁺ TLR7⁻ myeloid dendritic cells (Edwards A D, et al., *Eur J Immunol.* 2003; 33:827-833), thereby limiting efficacy. For this reason other compounds have been developed by modification of imiquimod.

Resiquimod is a potent dual TLR 7 and TLR 8 ligand (Wu J J, et al., *Antiviral Res.* 2004; 64:79-83). Since TLR 8 is expressed in CD8α⁺ myeloid dendritic cells, it has overcome one of the limitations of imiquimod (Coffman R L, et al., *Immunity* 2010; 33:492-503). Nonetheless, many factors have limited the efficacy of resiquimod and imiquimod. One recently identified mechanism for treatment failure is that although these drugs induce proinflamatory cytokines, they concurrently induce high levels of anti-inflammatory cytokines such as IL-10 (Gibson S J, et al., *Cell Immunol.* 2002; 218:74-86; and Lu H, et al., *J Immunol.* 2010; 184:5360-5367). Of clinical relevance, application of imiquimod cream works on the treated tumor, but not distal tumors, suggesting an impairment in systemic immunity (Lu H, et al., *J Immunol,* 2010:184:5360-5367; and Gill V L, et al., *Vet Comp Oncol.* 2008; 6:55-64). Indeed blockade of IL-10 following imiquimod treatment was shown to result in control of treated and distal (untreated) tumors, demonstrating the clinical significance of the self-regulating cytokine response induced by currently used Imidazoquinolines. Thus, a need exists to develop novel imquidazolequinoline-based compounds that trigger a more desirable ratio of pro- to anti-inflammatory cytokines.

As noted above, a related concept that has recently become clear is triggering multiple receptors is typically better for immune stimulation and triggering additional receptors might shift the cytokine prolife to a more desirable one. Two studies have shown that higher levels of IL1-β and IL-12 may be achieved by some TLR7/8 agonists, indicating that an alternative pathway exists for the selective induction of specific cytokines (Schiaffo et al. *J. Med. Chem.* 2014; 57:339-347; and Shi et al. *Med. Chem. Lett.* 2012; 3:501-504). The high levels of IL-1β suggest the additional receptor triggered by these compounds is the inflammasome. Since imiquimod (exclusive TLR7 ligand) and resiquimod (dual TLR7/8) ligand prime limited immunity, it would be desirable to develop improved compounds that tap additional receptors. In addition, agonists that selectively target TLR8 have been shown to induce Th1-polarizing cytokines which has significant advantages in the design of immunotherapies for treating cancer and infectious disease (Philbin and Levy, *Biochem. Soc. Trans.* 2007; 35:1485-1491). Finally, studies have indicated TLR agonists are suboptimally immunogenic unless they are directly conjugated to antigen (Kastenmuller K, et al., *J Clin Invest;* 121:1782-1796); thus new compounds that are amenable to conjugation should also be developed.

SUMMARY OF THE INVENTION

Imquidazolequinoline-based compounds that trigger a more desirable ratio of pro- to anti-inflammatory cytokines have been discovered. Accordingly there is provided a compound of the invention which is a compound of formula I:

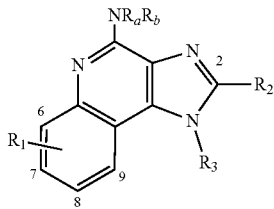

wherein:

$R_1$ is $R^k$—O—C(=O)-, $R^cR^dNC(=O)$—, $R^cR^dNS(O)_2$—, $R^eC(=O)N(R^e)$—, or $R^eS(O)_2NR^f$;

$R_2$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, $(C_3-C_6)$cycloalkyl, aryl, heteroaryl, heterocycle, $NR^gR^h$, or $R^mR^nNC(=O)$—, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, $(C_3-C_6)$cycloalkyl, aryl, heteroaryl, and heterocycle, is optionally substituted with one or more groups independently selected from the group consisting of the group consisting of hydroxy, halo, —SH, cyano, oxo, oxiranyl, $(C_3-C_8)$cycloalkyl, aryl, heteroaryl, $(C_1-C_6)$alkoxy, $(C_1-C_6)$alkylthio, and $NR^gR^h$;

$R_3$ is —$OR^z$ or $(C_1-C_6)$alkyl that is substituted with one or more groups independently selected from the group consisting of:

halo,
—$OR^z$,
—$N(H)S(O)_2R^r$,
$R^sC(=O)O$—,
aryl that is substituted with $(C_1-C_6)$alkyl that is substituted with heteroaryl, $NR^uR^v$, or one or more halo,
aryl that is substituted with halo, hydroxy, $(C_1-C_6)$alkoxy, —C(=O)$NR^uR^v$, or carboxy,
heteroaryl that is optionally substituted with $(C_1-C_6)$alkyl that is substituted with heteroaryl, $NR^uR^v$, or one or more halo,
heteroaryl that is optionally substituted with halo, $(C_1-C_6)$alkoxy, —C(=O)$NR^uR^v$, carboxy,
—S—$R^w$,
—$NR^xR^y$,
$(C_1-C_6)$alkoxycarbonyl, and
carboxy;

$R_a$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_3-C_6)$cycloalkyl, aryl, or heteroaryl, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_3-C_6)$cycloalkyl, aryl, and heteroaryl is optionally substituted with one or more groups independently selected from hydroxy, halo, —SH, cyano, oxiranyl, $(C_3-C_8)$cycloalkyl, aryl, heteroaryl, $(C_1-C_6)$alkoxy, $(C_1-C_6)$alkylthio, and $NR^gR^h$;

$R_b$ is H or X—Y;

each $R^c$ and $R^d$ is independently H, $(C_1-C_6)$alkyl, $(C_2-C_6)$alkenyl, $(C_3-C_8)$cycloalkyl, $(C_3-C_8)$cycloalkyl$(C_1-C_6)$alkyl, aryl, or aryl$(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^e$ is H or $(C_1-C_6)$alkyl;

$R^f$ is H or $(C_1-C_6)$alkyl;

each $R^g$ and $R^h$ is independently H, $(C_1-C_6)$alkyl, $(C_2-C_6)$alkenyl, $(C_3-C_8)$cycloalkyl, $(C_3-C_8)$cycloalkyl$(C_1-C_6)$alkyl, aryl, or aryl$(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^k$ is H, $(C_1-C_6)$alkyl, $(C_2-C_6)$alkenyl, $(C_2-C_6)$alkynyl, $(C_3-C_8)$cycloalkyl, trifluoromethyl, aryl, or aryl$(C_1-C_6)$alkyl, wherein each $(C_1-C_6)$alkyl can optionally be substituted with one or more halo, $(C_1-C_6)$alkanoyloxy, $(C_1-C_6)$alkoxy, $(C_3-C_8)$cycloalkyl;

each $R^m$ and $R^n$ is independently H, $(C_1-C_6)$alkyl, $(C_2-C_6)$alkenyl, $(C_3-C_8)$cycloalkyl, $(C_3-C_8)$cycloalkyl$(C_1-C_6)$alkyl, aryl, or aryl$(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

X is a linking group; and

Y is an antigen or maleimide;

wherein the tricyclic ring system in formula (I) can optionally be further substituted on one or more carbons with one or more groups independently selected from the group consisting of halo, hydroxy, nitro, $(C_1-C_6)$alkyl, $(C_1-C_6)$alkenyl, $(C_1-C_6)$alkynyl, $(C_1-C_6)$alkoxy, $(C_1-C_6)$alkanoyl, $(C_1-C_6)$alkanoyloxy, $(C_1-C_6)$alkoxycarbonyl, trifluoromethyl, trifluoromethoxy, cyano, and $NR^pR^q$; and each $R^p$ and $R^q$ is independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^r$ is H, aryl, or $(C_1-C_{10})$alkyl that is optionally substituted with halo or aryl;

$R^s$ is H, aryl, or $(C_1-C_{10})$alkyl that is optionally substituted with halo or aryl;

each $R^u$ and $R^v$ is independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^w$ is H, aryl, or $(C_1-C_{10})$alkyl that is optionally substituted with halo or aryl;

each $R^x$ and $R^y$ is independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl; and $R^z$ is H, aryl, or $(C_1-C_{10})$alkyl that is optionally substituted with halo or aryl;

or a salt thereof;

or a compound of formula I wherein:

$R_1$ is $R^{kk}$—C(=O)—, $R^{kk}$—S(O)$_2$—O—, or $R^{cc}SO_2$—NH—;

$R_2$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, $(C_3-C_6)$cycloalkyl, aryl, heteroaryl, heterocycle, $NR^{gg}R^{hh}$, or $R^{mm}R^{nn}NC(=O)$—, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, $(C_3-C_6)$cycloalkyl, aryl, heteroaryl, and heterocycle, is optionally substituted with one or more groups independently selected from the group consisting of hydroxy, halo, —SH, cyano, oxo, oxiranyl, $(C_3-C_8)$cycloalkyl, aryl, heteroaryl, $(C_1-C_6)$alkoxy, $(C_1-C_6)$alkylthio, and $NR^{gg}R^{hh}$;

$R_3$ is H, halo, hydroxy, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, $(C_3-C_6)$cycloalkyl, aryl, heteroaryl, heterocycle, $NR^{gg}R^{hh}$, or $R^{mm}R^{nn}NC(=O)$—, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, $(C_3-C_6)$cycloalkyl, aryl, heteroaryl, and heterocycle, is optionally substituted with one or more groups independently selected from the group consisting of halo,
cyano,
oxo,
oxiranyl,
$(C_3-C_8)$cycloalkyl,
aryl, that is optionally substituted with alkyl that is substituted with $NR^{uu}R^{vv}$,
aryl that is substituted with carboxy,
heteroaryl,
$(C_1-C_6)$alkoxy,
$(C_1-C_6)$alkylthio,
$OR^{zz}$,
—$N(H)S(O)_2R^{rr}$,
$R^{ss}C(=O)O$—,
—$S$—$R^{ww}$,
—$NR^{xx}R^{yy}$,
$(C_1-C_6)$alkoxycarbonyl, and
carboxy;

$R^a$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_3-C_6)$cycloalkyl, aryl, or heteroaryl, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_3-C_6)$cycloalkyl, aryl, and heteroaryl is optionally substituted with one or more groups independently selected from the group consisting of hydroxy, halo, —SH, cyano, oxiranyl, $(C_3-C_8)$cycloalkyl, aryl, heteroaryl, $(C_1-C_6)$alkoxy, $(C_1-C_6)$alkylthio, and $NR^{gg}R^{hh}$;

$R^b$ is H or X—Y;

$R^{cc}$ is aryl that is optionally substituted with one or more groups independently selected from the group consisting of hydroxy, halo, nitro, cyano, $(C_1-C_6)$alkoxy, and $(C_1-C_6)$alkyl that is optionally substituted with one or more halo;

each $R^{gg}$ and $R^{hh}$ is independently H, $(C_1-C_6)$alkyl, $(C_2-C_6)$alkenyl, $(C_3-C_8)$cycloalkyl, $(C_3-C_8)$cycloalkyl$(C_1-C_6)$alkyl, aryl, or aryl$(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^{kk}$ is H, $(C_1-C_6)$alkyl, $(C_2-C_6)$alkenyl, $(C_2-C_6)$alkynyl, $(C_3-C_8)$cycloalkyl, trifluoromethyl, aryl, or aryl$(C_1-C_6)$alkyl, wherein each $(C_1-C_6)$alkyl can optionally be substituted with one or more halo, $(C_1-C_6)$alkanoyloxy, $(C_1-C_6)$alkoxy, $(C_3-C_8)$cycloalkyl;

each $R^{mm}$ and $R^{nn}$ is independently H, $(C_1-C_6)$alkyl, $(C_2-C_6)$alkenyl, $(C_3-C_8)$cycloalkyl, $(C_3-C_8)$cycloalkyl$(C_1-C_6)$alkyl, aryl, or aryl$(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

X is a linking group; and
Y is an antigen or maleimide;

wherein the tricyclic ring system in formula (I) can optionally be further substituted on one or more carbons with one or more groups independently selected from the group consisting of halo, hydroxy, nitro, $(C_1-C_6)$alkyl, $(C_1-C_6)$alkenyl, $(C_1-C_6)$alkynyl, $(C_1-C_6)$alkoxy, $(C_1-C_6)$alkanoyl, $(C_1-C_6)$alkanoyloxy, $(C_1-C_6)$alkoxycarbonyl, trifluoromethyl, trifluoromethoxy, cyano, and $NR^{pp}R^{qq}$;

each $R^{pp}$ and $R^{qq}$ is independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^{rr}$ is H, aryl, or $(C_1-C_{10})$alkyl that is optionally substituted with halo or aryl;

$R^{ss}$ is H, aryl, or $(C_1-C_{10})$alkyl that is optionally substituted with halo or aryl;

each $R^{uu}$ and $R^{vv}$ is independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^{ww}$ is H, aryl, or $(C_1-C_{10})$alkyl that is optionally substituted with halo or aryl;

each $R^{xx}$ and $R^{yy}$ is independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl; and $R^{zz}$ is H, aryl, or $(C_1-C_{10})$alkyl that is optionally substituted with halo or aryl;

or a salt thereof;

or a compound of formula I wherein:

$R_1$ is $R^k$—O—C(=O)—, $R^cR^dNC(=O)$—, $R^cR^dNS(O)_2$—, $R^eC(=O)N(R^e)$—, or $R^eS(O)_2NR^f$;

$R_2$ is H, $NR^gR^h$, $(C_1-C_6)$alkanoyl, $(C_1-C_6)$alkoxycarbonyl, $(C_1-C_6)$alkanoyloxy, $R^mR^nNC(=O)$—, or $(C_1-C_6)$alkyl optionally substituted with one or more hydroxy, —SH, halo, oxiranyl, $(C_3-C_8)$cycloalkyl, aryl, $(C_1-C_6)$alkoxy, $(C_1-C_6)$alkylthio, or $NR^gR^h$;

$R_3$ is H;

$R_a$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_3-C_6)$cycloalkyl, aryl, or heteroaryl, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_3-C_6)$cycloalkyl, aryl, and heteroaryl is optionally substituted with one or more groups independently selected from hydroxy, halo, —SH, cyano, oxiranyl, $(C_3-C_8)$cycloalkyl, aryl, heteroaryl, $(C_1-C_6)$alkoxy, $(C_1-C_6)$alkylthio, and $NR^gR^h$;

$R_b$ is H or X—Y;

each $R^c$ and $R^d$ is independently H, $(C_1-C_6)$alkyl, $(C_2-C_6)$alkenyl, $(C_3-C_8)$cycloalkyl, $(C_3-C_8)$cycloalkyl$(C_1-C_6)$alkyl, aryl, or aryl$(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^e$ is H or $(C_1-C_6)$alkyl;

$R^f$ is H or $(C_1-C_6)$alkyl;

each $R^g$ and $R^h$ is independently H, $(C_1-C_6)$alkyl, $(C_2-C_6)$alkenyl, $(C_3-C_8)$cycloalkyl, $(C_3-C_8)$cycloalkyl$(C_1-C_6)$alkyl, aryl, or aryl$(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^k$ is H, $(C_1-C_6)$alkyl, $(C_2-C_6)$alkenyl, $(C_2-C_6)$alkynyl, $(C_3-C_8)$cycloalkyl, trifluoromethyl, aryl, or aryl$(C_1-C_6)$alkyl, wherein each $(C_1-C_6)$alkyl can optionally be substituted with one or more halo, $(C_1-C_6)$alkanoyloxy, $(C_1-C_6)$alkoxy, $(C_3-C_8)$cycloalkyl;

each $R^m$ and $R^n$ is independently H, $(C_1-C_6)$alkyl, $(C_2-C_6)$alkenyl, $(C_3-C_8)$cycloalkyl, $(C_3-C_8)$cycloalkyl$(C_1-C_6)$alkyl, aryl, or aryl$(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

X is a linking group; and

Y is an antigen or maleimide;

wherein the tricyclic ring system in formula (I) can optionally be further substituted on one or more carbons with one or more groups independently selected from the group consisting of halo, hydroxy, nitro, $(C_1-C_6)$alkyl, $(C_1-C_6)$alkenyl, $(C_1-C_6)$alkynyl, $(C_1-C_6)$alkoxy, $(C_1-C_6)$alkanoyl, $(C_1-C_6)$alkanoyloxy, $(C_1-C_6)$alkoxycarbonyl, trifluoromethyl, trifluoromethoxy, cyano, and $NR^pR^q$; and each $R^p$ and $R^q$ is independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

or a salt thereof.

The invention also provides a pharmaceutical composition comprising a compound of formula I, or a pharmaceutically acceptable salt thereof, and a pharmaceutically acceptable diluent or carrier.

The invention also provides a method for treating a pathological condition (e.g. a viral infection, a bacterial infection or cancer) in an animal comprising administering a compound of formula I, or a pharmaceutically acceptable salt thereof, to the animal.

The invention also provides a method for stimulating an immune response in an animal comprising administering a compound of formula I, or a pharmaceutically acceptable salt thereof, to the animal.

The invention provides a compound of formula I or a pharmaceutically acceptable salt thereof for use in the prophylactic or therapeutic treatment of a pathological condition (e.g. a viral infection, a bacterial infection or cancer) in an animal.

The invention provides a compound of formula I or a pharmaceutically acceptable salt thereof for use in medical therapy.

The invention provides the use of a compound of formula I or a pharmaceutically acceptable salt thereof for the manufacture of a medicament useful for the treatment of a pathological condition (e.g. a viral infection, a bacterial infection or cancer) in an animal.

The invention also provides processes and intermediates disclosed herein that are useful for preparing compounds of formula (I) or salts thereof.

Certain compounds of the invention may be particularly useful because they may be selective for TLR-7 over other toll-like receptors, such as, for example, TLR-8.

Certain compounds of the invention may be particularly useful because they selectively activate TLR7 or TLR8 or alternate receptors (such as the inflammasome) in triggering the productions of specific cytokines.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term "heterocycle" refers to a single saturated or partially unsaturated ring or a multiple condensed ring system. The term includes single saturated or partially unsaturated rings (e.g. 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g. ring systems comprising 2, 3 or 4 rings) wherein a single heterocycle ring (as defined above) can be condensed with one or more heterocycles (e.g. decahydronapthyridinyl), carbocycles (e.g. decahydroquinolyl) or aryls. The rings of a multiple condensed ring system can be connected to each other via fused, spiro and bridged bonds when allowed by valency requirements. It is to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g. a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

The term "treatment" or "treating," to the extent it relates to a disease or condition includes preventing the disease or condition from occurring, inhibiting the disease or condition, eliminating the disease or condition, and/or relieving one or more symptoms of the disease or condition.

In one embodiment of the invention $R_1$ is $R^cR^dNS(O)_2$— or $R^eS(O)_2NR^f$— when $R_2$ is $NR^gR^h$.

In one embodiment of the invention $R_1$ is $R^cR^dNS(O)_2$— or $R^eS(O)_2NR^f$— when $R_2$ is ($C_1$-$C_6$)alkyl substituted with one or more ($C_1$-$C_6$)alkylthio.

Linking Group X

In certain embodiments of the invention X is a linking group that joins the remainder of the compound of formula I to an antigen or to a maleimide. Compounds wherein Y is a maleimide are useful as intermediates for preparing compounds wherein Y is an antigen. The nature of the linking group X is not critical provided the resulting antigen conjugate retains the useful biological propertied described herein.

In one embodiment of the invention the linker has a molecular weight of from about 20 daltons to about 20,000 daltons.

In one embodiment of the invention the linker has a molecular weight of from about 20 daltons to about 5,000 daltons.

In one embodiment of the invention the linker has a molecular weight of from about 20 daltons to about 1,000 daltons.

In one embodiment of the invention the linker has a molecular weight of from about 20 daltons to about 200 daltons.

In another embodiment of the invention the linker has a length of about 5 angstroms to about 60 angstroms.

In another embodiment of the invention the linker separates the antigen from the remainder of the compound of formula I by about 5 angstroms to about 40 angstroms, inclusive, in length.

In another embodiment of the invention the linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In another embodiment of the invention the linker comprises a polyethyleneoxy chain. In another embodiment of the invention the polyethyleneoxy chain comprises 2, 3, 4, 5, 6, 7, 8, 9, or 10 repeating ethyleneoxy units.

In another embodiment of the invention the linker is a divalent radical formed from a protein.

In another embodiment of the invention the linker is a divalent radical formed from a peptide.

In another embodiment of the invention the linker is a divalent radical formed from an amino acid.

In another embodiment the linker is:

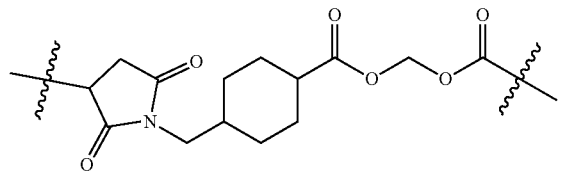

-continued

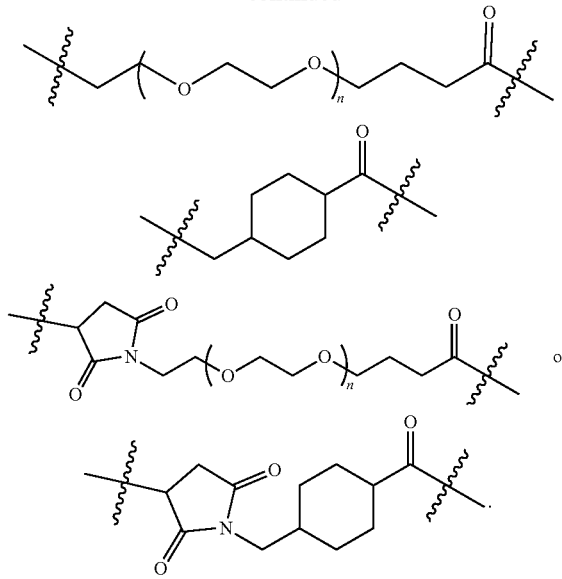

In another embodiment of the invention the linker is:

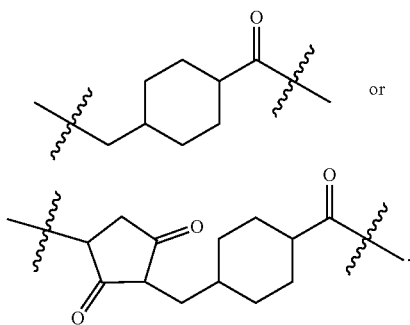

Antigen

An "antigen" as used herein includes any substance that causes the immune system to produce antibodies or antigen-specific T cells against the substance. The term also includes haptans. An antigen may be a foreign substance from the environment such as a chemical, bacteria, virus, or pollen. An antigen may also be formed within the body such as with bacterial toxins, tissue cells, or tumor cells. The antigen is the molecular structure encoded by the substance such as the pathogen or tumor against which the immune response is directed. Examples of antigens may come from pathogens such as bacteria or viruses (e.g. influenza, HIV, or HCV) Alternatively, the antigen may come from a tumor cell or a tumor cell lysate or synthetic peptides derived from tumors or infectious organisms. In one embodiment the antigen comprises a peptide sequence containing cysteine or lysine.

Processes for preparing compounds of formula I are provided as further embodiments of the invention and are illustrated by the following procedures in which the meanings of the generic radicals are as given above unless otherwise qualified. Certain compounds of formula I are useful as intermediates for preparing other compounds of formula I.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Example 1. Preparation of Compound 571(S7)

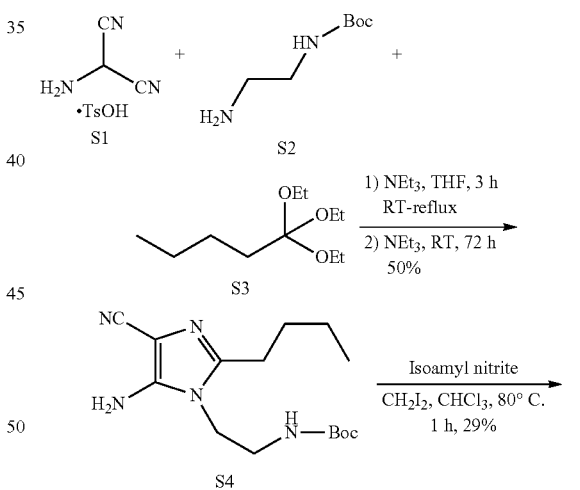

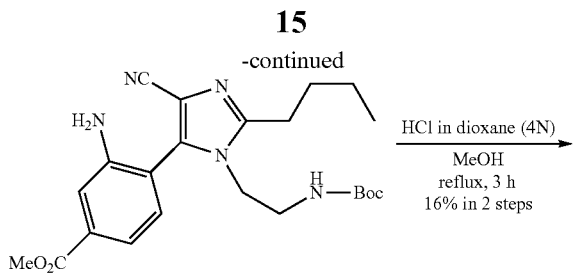

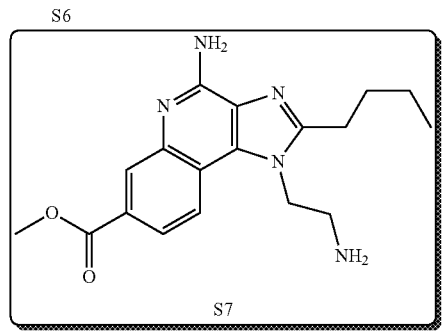

a. 5-Amino-1-{2-[(tert-butoxycarbonyl)amino]ethyl}-2-butyl-1H-imidazole-4-carbonitrile (S4)

To a suspension of aminomalononitrile p-toluenesulfonate (2.0 g, 7.9 mmol, 1.0 equiv) in THF (60 mL) at 25° C. was added NEt$_3$ (1.8 mL, 13 mmol, 1.6 equiv) in one portion. The mixture was stirred for 30 min to afford a homogeneous solution. To this solution was added triethyl orthovalerate S3 (2.55 g, 15.7 mmol, 2 equiv) and the solution was heated at reflux under N$_2$ for 3 h then cooled to 25° C. Next, NEt$_3$ (1.8 mL, 13 mmol, 1.6 equiv) and tert-butyl N-(2-aminoethyl)carbamate S2 (1.46 g, 14.2 mmol, 1.8 equiv) were added sequentially and the reaction was stirred at 25° C. for 72 h. The reaction was concentrated in vacuo and the resulting solid residue was redissolved in CH$_2$Cl$_2$ (40 mL) and washed with saturated aqueous Na$_2$CO$_3$ solution (25 mL). The aqueous layer was extracted with CH$_2$Cl$_2$ (3'15 mL). The combined organic fractions were washed with saturated aqueous NaCl, dried (MgSO$_4$) and concentrated in vacuo. Purification by flash column chromatography on silica gel (40/60 EtOAc/hexanes-75/25 EtOAc/hexanes, gradient) afforded the title compound (1.22 g, 50.2%) as an off white solid: $^1$H NMR (CDCl$_3$, 400 MHz) δ 0.90 (t, J=7.4 Hz, 3H), 1.35 (hex, J=7.4 Hz, 2H), 1.42 (s, 9H), 1.64 (quin, J=7.4 Hz, 2H), 2.50 (t, J=7.8 Hz, 2H), 3.31 (q, J=6.6 Hz, 2H), 3.86 (t, J=6.6 Hz, 2H), 4.63 (br s, 2H), 5.42 (br s, 1H).

b. 1-{2-[(tert-butoxycarbonyl)amino]ethyl}-2-butyl-5-iodo-1H-imidazole-4-carbonitrile (S5)

To a solution of 5-Amino-1-{2-[(tert-butoxycarbonyl)amino]ethyl}-2-butyl-1H-imidazole-4-carbonitrile S4 (1.05 g, 3.42 mmol, 1.0 equiv) and CH$_2$I$_2$ (11.8 g) in CHCl$_3$ (20 mL) was added a solution of isoamylnitrite (2.5 g, 21.3 mmol, 6.25 equiv) in CHCl$_3$ (5 mL) over 1 min. The reaction was stirred for 1 h at 80° C. under N$_2$ then cooled to 25° C. The reaction was concentrated in vacuo and purification by silica gel column chromatography (hexanes-55/45 EtOAc/hexanes, gradient) afforded the title compound (412 mg, 28.8%) as a copper solid: $^1$H NMR (CDCl$_3$, 400 MHz) δ 0.94 (t, J=7.4 Hz, 3H), 1.41 (hex, J=7.4 Hz, 2H), 1.43 (s, 9H), 1.73 (quin, J=7.4 Hz, 2H), 2.74 (t, J=7.8 Hz, 2H), 3.40 (q, J=5.9 Hz, 2H), 4.08 (t, J=5.9 Hz, 2H), 4.77 (s, 1H).

c. 5-(2-Amino-4-methoxycarbonylphenyl)-1-{2-[(tert-butoxycarbonyl)amino]ethyl}-2-butyl-1H-imidazole-4-carbonitrile (S6)

To a solution of 1-{2-[(tert-butoxycarbonyl)amino]ethyl}-2-butyl-5-iodo-1H-imidazole-4-carbonitrile S5 (343 mg, 0.82 mmol, 1 equiv) and 2-amino-4-methoxycarbonylphenylboronic acid pinacol ester (980 mg, 3.5 mmol, 4.3 equiv) in THF (25 mL) were sequentially added Pd(PPh$_3$)$_2$Cl$_2$ (87 mg, 0.124 mmol, 0.15 equiv), K$_2$CO$_3$ (520 mg, 3.76 mmol, 4.6 equiv), and water (10 mL) at 25° C. The reaction was heated at 90° C. for 2 h. TLC analysis indicated the presence of S6. S5 starting material appeared to be absent. The reaction was then cooled down to 25° C. and partitioned between EtOAc (20 mL) and H$_2$O (20 mL). The aqueous layer was extracted with EtOAc (3'15 mL). The combined organic layers were concentrated in vacuo. Purification by flash column chromatography on silica gel (50/50 EtOAc/hexanes-90/10 EtOAc/hexanes, gradient) afforded the title compound (~195 mg, ~90% pure by TLC) as light copper oil, some of which was used in the next step without further purification.

d. 4-Amino-1-(2-aminoethyl)-2-butyl-7-methoxycarbonyl-1H-imidazo[4,5-c]quinoline (S7) (S71)

5-(2-Amino-4-methoxycarbonylphenyl)-1-{2-[(tert-butoxycarbonyl)amino]ethyl}-2-butyl-1H-imidazole-4-carbonitrile S6 (~65 mg, ~90% pure) was dissolved in anhydrous methanol (2 mL) and stirred at 60° C. under N$_2$. After 5 mn, 4 N HCl in dioxane (4.0 mL, 16.0 mmol, ~120 equiv) was added and the reaction was heated at reflux for 3 h then cooled to 25° C. The reaction was quenched with solid NaHCO$_3$ (1.5 g), diluted with EtOAc (10 mL), then water (10 mL) and separated. The aqueous layer was extracted with 1:9 MeOH/EtOAc (3'10 mL). The combined organic layers were dried (MgSO$_4$), and concentrated in vacuo. Purification by flash column chromatography on silica gel (EtOAc-6/7/7/80 H$_2$O/MeOH/NEt$_3$/EtOAc, gradient) afforded the title compound (15 mg, 16% over 2 steps) as a white solid: $^1$H NMR (CD$_3$OD, 400 MHz) δ 1.02 (t, J=7.4 Hz, 3H), 1.53 (hex, J=7.4 Hz, 2H), 1.89 (quin, J=7.4, 2H), 3.02 (t, J=7.4 Hz, 2H), 3.11 (t, J=7.4 Hz, 2H), 3.93 (s, 3H), 4.61 (t, J=7.4 Hz, 2H), 7.89 (dd, J=8.6, 1.6 Hz, 1H), 8.17 (d, J=8.6 Hz, 1H), 8.32 (d, J=1.6 Hz, 1H).

Using procedures similar to those described in Example 1 and procedures that are known, for example see U.S. Pat. No. 9,034,336, the following representative compounds of Formula (I) were also prepared.

| Compound Number | Structure | Characterization |
|---|---|---|
| 539 | 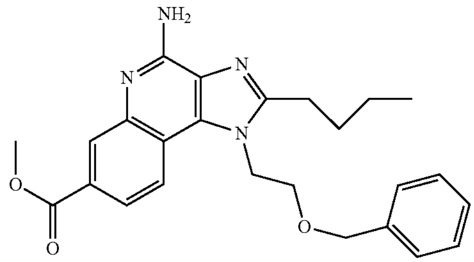 | ¹H (DMF-d7, 400 MHz) δ 8.19 (s, 1H), 8.07, (d, J = 8.2 Hz, 1H), 7.62 (d, J = 7.4, 8.4 Hz, 1H), 7.44 (t, J = 8.0 Hz, 1H), 7.28-7.09 (m, 5H), 6.70 (s, 2H), 4.89 (t, J = 4.8 Hz, 2H), 4.45 (s, 2H), 3.89 (t, J = 4.8 Hz, 2H); ¹³C (DMF-d7, 100 MHz) δ 153.4, 145.9, 144.7, 139.5, 133.5, 129.5, 129.3, 128.5, 128.4, 128.0, 127.3, 122.5, 121.9, 116.4, 73.4, 69.4, 48.1; HRMS (APCI+): calcd C₁₉H₁₉N₄O [M + H]⁺ 319.1553, found 319.1562 (error 2.78 ppm). |
| 544 | 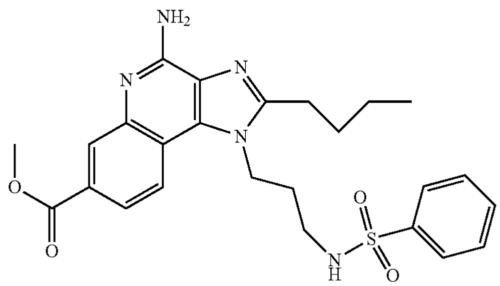 [SMILES: CCCCc1nc2c(N)nc3cc(C(=O)OC)ccc3c2n1CCCNS(=O)(=O)c1ccccc1] | ¹H (DMSO-d6, 400 MHz) δ 8.22-8.12 (m, 2H), 7.90-7.82 (m, 1H), 7.81-7.71 (m, 3H), 7.66-7.52 (m, 3H), 6.72 (s, 2H), 4.54 (t, J = 7.4 Hz, 2H), 3.90 (s, 3H), 3.00-2.84 (m, 4H), 1.97-1.86 (m, 2H), 1.77 (p, J = 7.4 Hz, 2H), 1.43 (sextet, J = 7.4 Hz, 2H), 0.95 (t, J = 7.4 Hz, 3H); ¹³C (DMSO-d6, 100 MHz) δ 166.5, 154.3, 152.4, 144.0, 140.1, 132.4, 121.6, 129.2, 127.8, 127.5, 127.0, 126.4, 120.7, 120.6, 117.8, 52.1, 42.4, 29.9, 29.6, 26.1, 21.9, 13.8; HRMS (APCI+): calcd C₂₅H₃₀N₅O₄S [M + H]⁺ 496.2013, found 496.2016 (error 0.54 ppm). |
| 546 | 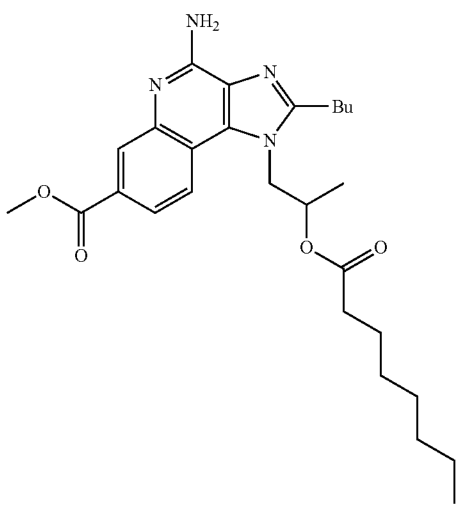 | ¹H (CDCl₃, 400 MHz) δ 8.52 (d, J = 1.8 Hz, 1H), 8.07 (d, J = 8.8 Hz, 1H), 7.95 (dd, J = 1.8, 8.6 Hz, 1H), 5.51 (s, 2H), 5.44-5.34 (m, 1H), 4.68 (dd, J = 9.4, 15.5 Hz, 1H), 4.51 (dd, J = 4.1, 15.5 Hz, 1H), 3.97 (s, 3H), 3.04-2.89 (m, 2H), 2.11-1.89 (m, 4H), 1.54 (sextet, J = 7.6 Hz, 2H), 1.49 (d, J = 6.3 Hz, 3H), 1.38-0.99 (m, 13H), 0.89 (t, J = 7.2 Hz, 3H). |
| 549 | 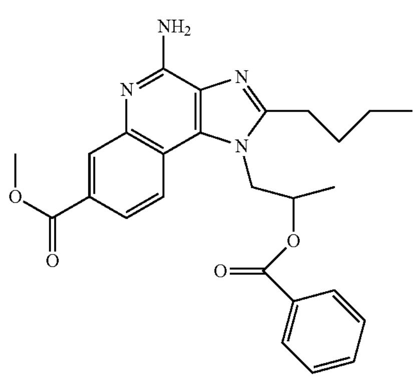 [SMILES: CCCCc1nc2c(N)nc3cc(C(=O)OC)ccc3c2n1CC(C)OC(=O)c1ccccc1] | ¹H (CDCl₃, 400 MHz) δ 8.51 (s, 1H), 8.16 (d, J = 8.6 Hz, 1H), 7.99 (d, J = 8.6 Hz, 1H), 7.79 (d, J = 8.0 Hz, 2H), 7.50 (t, J = 7.6 Hz, 1H), 7.32 (t, J = 7.6 Hz, 2H), 5.72-5.61 (m, 1H), 5.45 (s, 2H), 4.86 (dd, J = 8.8, 15.5 Hz, 1H), 4.66 (dd, J = 4.3, 15.5 Hz, 1H), 3.98 (s, 3H), 3.07-2.90 (m, 2H), 1.99-1.75 (m, 2H), 1.55 (d, J = 6.3 Hz, 3H), 1.51 (sextet, J = 7.4 Hz, 2H), 1.00 (t, J = 7.4 Hz, 3H); ¹³C (CDCl₃, 100 MHz) δ 167.2, 165.5, 154.8, 151.6, 144.2, 133.3, 133.0, 129.4, 129.2, 128.3, 128.1, 122.3, 119.6, 118.4, 69.5, 52.2, 49.5, 29.8, 27.3, 22.6, 17.9, 13.8; HRMS (APCI+): calcd C₂₆H₂₉N₄O₄ [M + H]⁺ 461.2183, found 461.2176 (error 1.48 ppm). |

| Compound Number | Structure | Characterization |
|---|---|---|
| 556 | 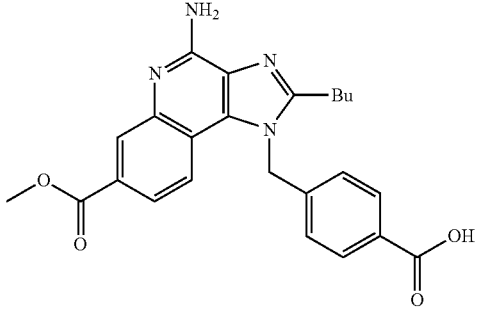 | ¹H NMR (DMSO-d6, 400 MHz) δ 0.80 (t, J = 7.5 Hz, 3H), 1.33 (hex, J = 7.5 Hz, 2H), 1.66 (quin, J = 7.5 2H), 2.93 (t, J = 7.5 Hz, 2H), 3.11 (s, 2H), 3.83 (s, 3H), 6.02 (s, 2H), 7.15 (d, J = 7.8, 2H), 7.69 (d, J = 8.2 Hz, 1H), 7.84 (d, J = 7.8 Hz, 2H), 7.95 (d, J = 8.2, 1H), 8.28 (s, 1H). |
| 557 | 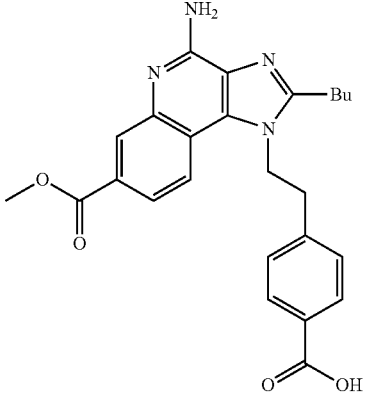 | ¹H NMR (CD₃OD, 400 MHz) δ 0.87 (t, J = 7.4 Hz, 3H), 1.29 (hex, J = 7.4 Hz, 2H), 1.63 (quin, J = 7.4, 2H), 2.38 (t, J = 7.5 Hz, 2H), 3.33 (t, J = 6.3, 2H), 3.99 (s, 3H), 4.93 (t, J = 6.3, 2H), 7.06 (d, J = 8.2, 2H), 7.85 (d, J = 8.2, 2H), 8.19 (d, J = 9 Hz, 1H) 8.42 (s, 1H), 8.43 (d, J = 9 Hz, 1H). |
| 558 | 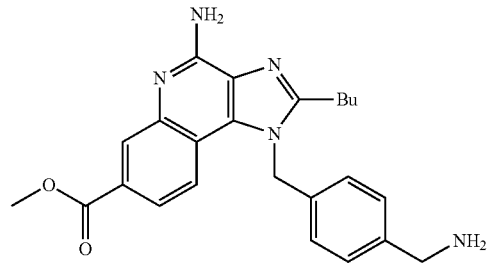 | ¹H NMR (CD₃OD, 400 MHz) δ 0.93 (t, J = 7.4 Hz, 3H), 1.44 (hex, J = 7.4 Hz, 2H), 1.79 (quin, J = 7.4 2H), 2.98 (t, J = 7.4 Hz, 2H), 3.79 (s, 2H), 3.90 (s, 3H), 5.88 (s, 2H), 7.03 (d, J = 7.8 Hz, 2H), 7.32 (d, J = 7.8 Hz, 2H), 7.61 (d, J = 9 Hz, 1H), 7.83 (d, J = 9 Hz, 1H), 8.29 (s, 1H). |
| 563 | 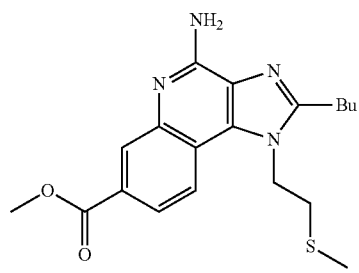 | ¹H NMR (CDCl₃, 400 MHz) δ 1.02 (t, J = 7.4 Hz, 3H), 1.52 (hex, J = 7.4, 2H), 1.89 (quin, J = 7.4 Hz, 2H), 2.13 (s, 3H), 2.99 (t, J = 7.4 Hz, 2H), 3.01 (t, J = 7.4 Hz, 2H), 3.97 (s, 3H), 4.68 (t, J = 7.4 Hz, 2H), 6.03 (br s, 2H), 7.96 (s, 2H), 8.53 (s, 1H). |
| 564 | 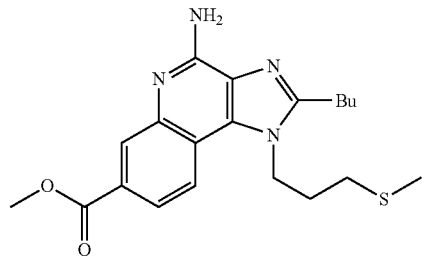 | ¹H NMR (CDCl₃, 400 MHz) δ 1.02 (t, J = 7.4 Hz, 3H), 1.52 (hex, J = 7.4, 2H), 1.89 (quin, J = 7.4 Hz, 2H), 2.18 (s, 3H), 2.21 (tt, J = 6.3, 7.8 Hz, 2H), 2.65 (t, J = 6.3 Hz, 2H) 2.96 (t, J = 7.4 Hz, 2H), 3.97 (s, 3H), 4.62 (t, J = 7.8 Hz, 2H), 5.45 (br s, 2H), 7.94 (dd, J = 8.6, 1.6 Hz, 1H), 8.11 (d, J = 8.6 Hz, 1H), 8.52 (d, J = 1.6 Hz, 1H). |

-continued

| Compound Number | Structure | Characterization |
|---|---|---|
| 565 | 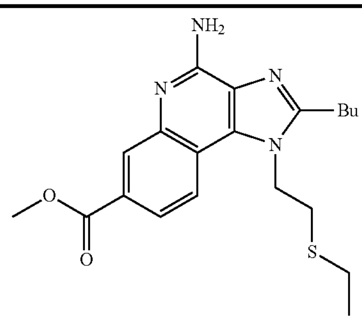 | ¹H NMR (CDCl₃, 400 MHz) δ 1.01 (t, J = 7.4 Hz, 3H), 1.24 (t, J = 7.4 Hz, 3H), 1.52 (hex, J = 7.4, 2H), 1.88 (quin, J = 7.4 Hz, 2H), 2.54 (q, J = 7.4 Hz, 2H), 2.97 (t, J = 7.4 Hz, 2H), 3.02 (t, J = 7.4 Hz, 2H), 3.96 (s, 3H), 4.65 (t, J = 7.4 Hz, 2H), 5.53 (br s, 2H), 7.94 (s, 2H), 8.52 (s, 2H). |
| 566 | 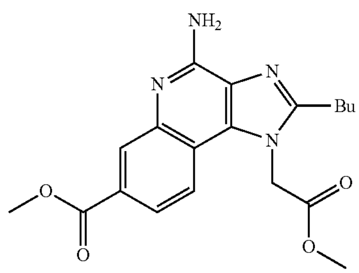 | ¹H NMR (CDCl₃, 400 MHz) δ 0.98 (t, J = 7.4 Hz, 3H), 1.48 (hex, J = 7.4, 2H), 1.84 (quin, J = 7.4 Hz, 2H), 2.87 (t, J = 7.4 Hz, 2H), 3.81 (s, 3H), 3.94 (s, 3H), 5.27 (s, 2H), 6.48 (br s, 2H), 7.78 (d, J = 8.2 Hz, 1H), 7.95 (dd, J = 8.2, 1.6 Hz, 1H), 8.42 (d, J = 1.6 Hz, 1H). |
| 567 | 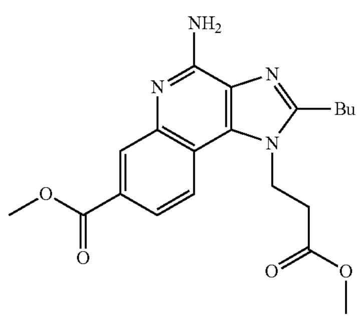 | ¹H NMR (CDCl₃, 400 MHz) δ 1.01 (t, J = 7.4 Hz, 3H), 1.52 (hex, J = 7.4, 2H), 1.85 (quin, J = 7.4 Hz, 2H), 2.95 (t, J = 7.4 Hz, 2H), 2.97 (t, J = 7.4 Hz, 2H), 3.74 (s, 3H), 3.96 (s, 3H), 4.81 (t, J = 7.4 Hz, 2H), 5.50 (br s, 2H), 7.96 (s, 2H), 8.53 (s, 1H). |
| 568 | 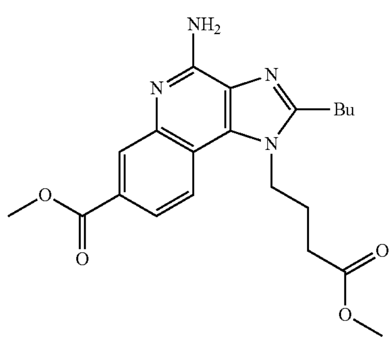 | ¹H NMR (CDCl₃, 400 MHz) δ 1.01 (t, J = 7.4 Hz, 3H), 1.52 (hex, J = 7.4, 2H), 1.88 (quin, J = 7.4 Hz, 2H), 2.23 (quin, J = 6.8 Hz, 2H), 2.52 (t, J = 6.8 Hz, 2H), 2.93 (t, J = 7.4 Hz, 2H), 3.74 (s, 3H), 3.96 (s, 3H), 4.55 (t, J = 6.8 Hz, 2H), 5.43 (br s, 2H), 7.96 (d, J = 8.6 Hz, 1H), 8.07 (d, J = 8.6 Hz, 1H), 8.52 (s, 1H). |
| 569 | 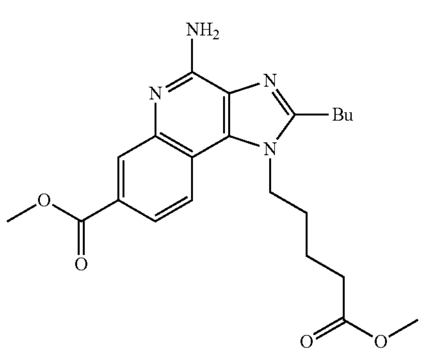 | ¹H NMR (CDCl₃, 400 MHz) δ 1.01 (t, J = 7.4 Hz, 3H), 1.52 (hex, J = 7.4, 2H), 1.76-1.91 (m, 4H), 1.97 (quin, J = 7.4 Hz, 2H), 2.40 (t, J = 7.4 Hz, 2H), 2.92 (t, J = 7.4 Hz, 2H), 3.66 (s, 3H), 3.97 (s, 3H), 4.47 (t, J = 7.4 Hz, 2H), 5.46 (br s, 2H), 7.95 (s, 2H), 8.52 (s, 1H). |

-continued

| Compound Number | Structure | Characterization |
|---|---|---|
| 570 | 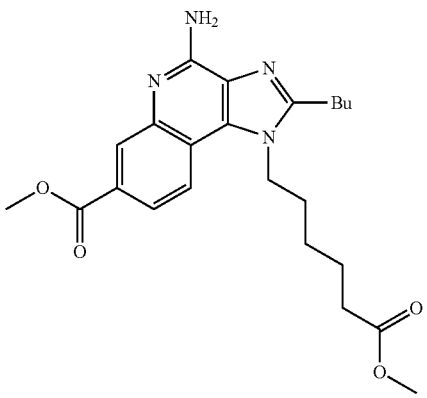 | ¹H NMR (CDCl₃, 400 MHz) δ 0.97 (t, J = 7.4 Hz, 3H), 1.40-1.55 (m, 4H), 1.68 (quin, J = 7.4 Hz, 2H), 1.76-1.96 (m, 4H), 2.31 (t, J = 7.0 Hz, 2H), 2.85 (t, J = 7.4 Hz, 2H), 3.64 (s, 3H), 3.93 (s, 3H), 4.36 (t, J = 7.4 Hz, 2H), 5.90 (br s, 2H), 7.84 (m, 2H), 8.44 (s, 1H). |
| 572 | 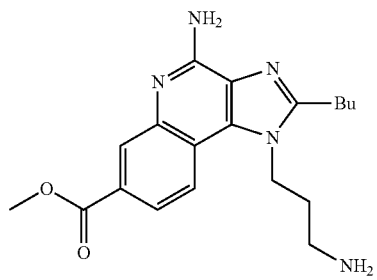 | ¹H NMR (CD₃OD, 400 MHz) δ 1.03 (t, J = 7.4 Hz, 3H), 1.53 (hex, J = 7.4 Hz, 2H), 1.89 (quin, J = 7.4, 2H), 2.19 (quin, J = 7.4, 2H), 2.99 (t, J = 7.4 Hz, 2H), 3.05 (t, J = 7.4 Hz, 2H), 3.94 (s, 3H), 4.67 (t, J = 7.4 Hz, 2H), 7.90 (d, J = 8.6 Hz, 1H), 8.13 (d, J = 8.6 Hz, 1H), 8.31 (s, 1H). |
| 573 | 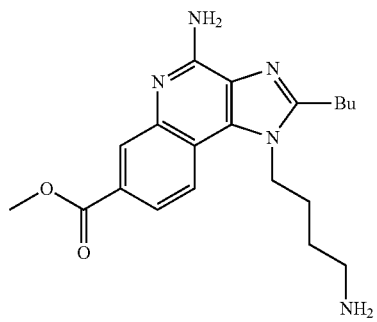 | ¹H NMR (CD₃OD, 400 MHz) δ 1.04 (t, J = 7.4 Hz, 3H), 1.54 (hex, J = 7.4 Hz, 2H), 1.65 (quin, J = 7.4 Hz, 2H), 1.85-2.00 (m, 4H), 2.70 (t, J = 6.6 Hz, 2H), 3.02 (t, J = 7.4 Hz, 2H), 3.96 (s, 3H), 4.61 (t, J = 7.4 Hz, 2H), 7.93 (d, J = 8.6 Hz, 1H), 8.15 (d, J = 8.6 Hz, 1H), 8.36 (s, 1H). |
| 574 | 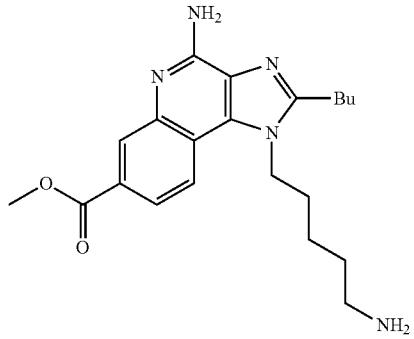 | ¹H NMR (CD₃OD, 400 MHz) δ 1.03 (t, J = 7.4 Hz, 3H), 1.46-1.62 (m, 6H), 1.82-1.98 (m, 4H), 2.69 (t, J = 6.6 Hz, 2H), 2.98 (t, J = 7.4 Hz, 2H) 3.95 (s, 3H), 4.55 (t, J = 7.4 Hz, 2H), 7.89 (d, J = 8.6 Hz, 1H), 8.08 (d, J = 8.6 Hz, 1H), 8.33 (s, 1H). |

| Compound Number | Structure | Characterization |
|---|---|---|
| 575 | 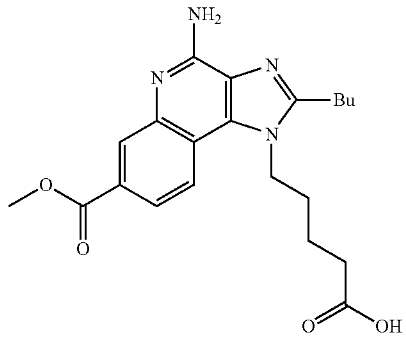 | |
| 576 | 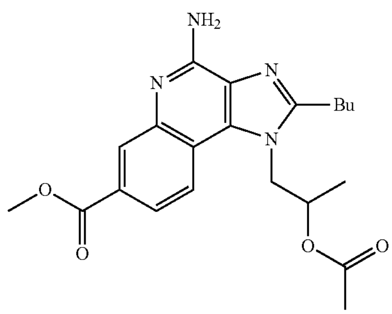 | |
[a] HEK SEAP Reporter Assay.
[c] N/A = no activity
Example 2. Preparation of Compound S8 (548)
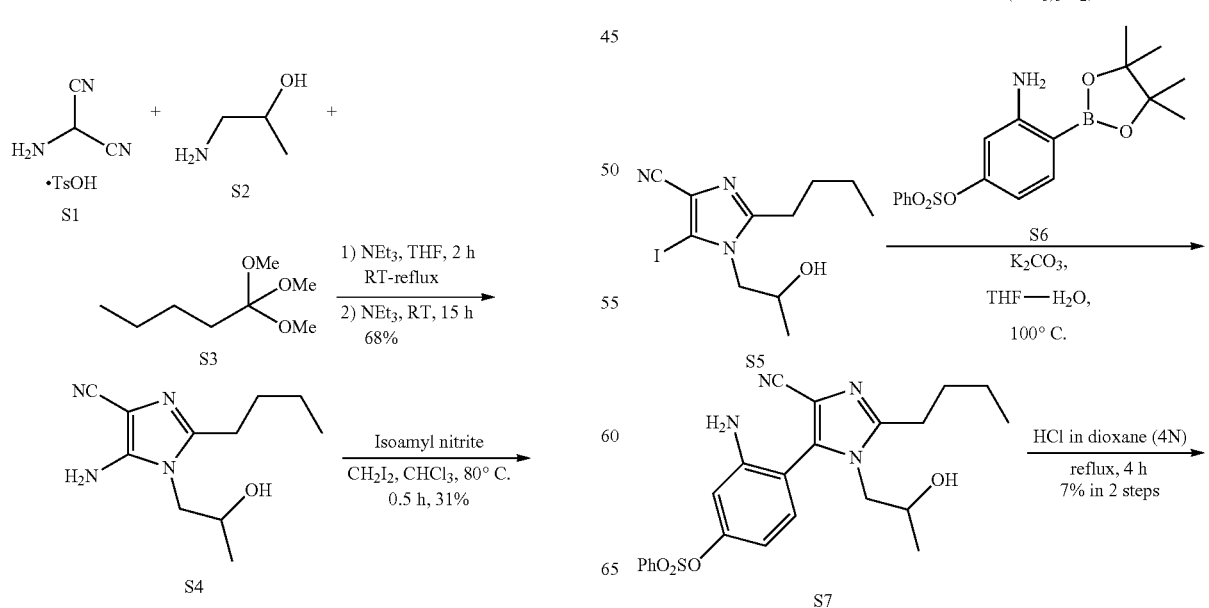

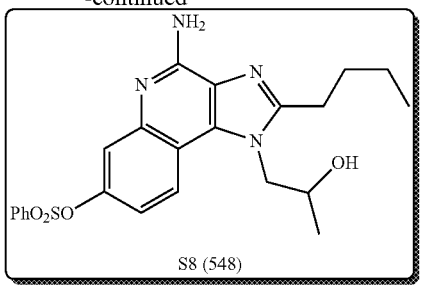

S8 (548)

a. 5-Amino-2-butyl-1-(2-hydroxypropyl)-1H-imidazole-4-carbonitrile (S4)

To a suspension of aminomalononitrile p-toluenesulfonate (4 mmol, 1.0 equiv) in THF (30 mL) at 25° C. was added $NEt_3$ (4.8 mmol, 1.2 equiv) in one portion. The mixture was stirred for 30 min to afford a homogeneous solution. To this solution was added triethyl orthovalerate S3 (4.8 mmol, 1.2 equiv) and the solution was heated at reflux for 3 h and then cooled to 25° C. Next, $NEt_3$ (4.8 mmol, 1.2 equiv) and 1-amino-2-propanol S2 (4.8 mmol, 1.2 equiv) were added sequentially and the reaction was stirred at 25° C. for 15 h. The reaction was concentrated in vacuo and the resulting solid residue was redissolved in $CH_2Cl_2$ (100 mL) and washed with saturated aqueous $Na_2CO_3$ solution (25 mL). The aqueous layer was extracted with $CH_2Cl_2$ (3×20 mL). The combined organic fractions were washed with saturated aqueous NaCl, dried ($MgSO_4$) and concentrated in vacuo. Purification by flash column chromatography on silica gel afforded the title compound (68%) as a beige solid: $R_f$ 0.8 (EtOAc); $^1$H NMR ($CDCl_3$, 400 MHz) δ 4.45 (s, 2H), 4.23-4.14 (m, 1H), 3.78 (dd, J=15.0, 2.54 Hz, 1H), 3.67 (dd, J=15.0, 9.1 Hz, 1H), 3.45 (s, 1H), 2.50 (dt, J=7.2, 2.7 Hz, 2H), 1.73-1.63 (m, 2H), 1.40 (hex, J=7.4 Hz, 2H), 1.33 (d, J=6.3 Hz, 3H), 0.94 (t, J=7.4 Hz, 3H); $^{13}$C NMR ($CDCl_3$, 100 MHz): δ 148.3, 143.3, 118.0, 88.4, 65.1, 49.2, 28.5, 25.9, 21.8, 20.9, 13.8; HRMS (APCI+): calcd $C_{11}H_{19}N_4O$ $[M+H]^+$ 223.1553. found 223.1557 (error 1.5 ppm).

b. 2-Butyl-1-(2-hydroxypropyl)-5-iodo-1H-imidazole-4-carbonitrile (S5)

To a solution of 5-amino-2-butyl-1-(2-hydroxypropyl)-1H-imidazole-4-carbonitrile S4 (2.5 mmol, 1.0 equiv) and $CH_2I_2$ (5.0 mL) at 80° C. was added a solution of isoamylnitrite (10.2 mmol, 4.0 equiv) in $CHCl_3$ (5 mL) over 20 min. The reaction was stirred for additional 30 min at 80° C. then cooled to 25° C. The reaction was concentrated in vacuo and purification by silica gel column chromatography (1/9 EtOAc/hexanes-7/3 EtOAc/hexanes, gradient) afforded the title compound (31%) as an amber solid: $R_f$ 0.33 (50:50, EtOAc/hexanes); $^1$H NMR ($CDCl_3$, 400 MHz) δ 4.24-4.14 (m, 1H), 3.94-3.82 (m, 2H), 2.88-2.72 (m, 2H), 2.19 (d, J=3.7 Hz, 1H), 1.73 (p, J=7.43 Hz, 2H), 1.41 (hex, J=7.4 Hz, 2H), 1.35 (d, J=6.2 Hz, 3H), 0.95 (t, J=7.4 Hz, 3H); $^{13}$C NMR (400 MHz, $CDCl_3$): δ 154.5, 120.6, 114.8, 81.6, 66.8, 54.4, 29.3, 27.7, 22.3, 21.0, 13.7; HRMS (APCI+): calcd $C_{11}H_{17}IN_3O$ $[M+H]^+$ 334.0411. found 334.0406 (error 1.45 ppm).

c. 3-amino-4-(4,4,5,5-tetramethyl-1,3,2-dioxaborolan-2-yl)phenyl benzenesulfonate (S6)

To a vial containing 4-Iodo-3-nitrophenylbenzenesulfonate* (891 mg, 2.4 mmol, 1 equiv), Bis(pinacolato)diboron (723 mg, 2.9 mmol, 1.2 equiv), Pd(dppf)Cl₂ (87 mg, 0.1 mmol, 0.05 equiv), and KOAc (705 mg, 7.2 mmol, 3 equiv) was added DMSO (8 mL, 0.3M) and heated at 80° C. for 16 hrs. After which the reaction was filtered thru celite and the residue washed with $H_2O$ (20 mL) and EtOAc (2×100 mL). The organic layer was concentrated in vacuo and the crude residue was flashed thru a silica plug with 30:70-60:40 EtOAc/hex and carried on directly to the next step.

d. 5-(2-Amino-4-benzenesulfonyl)-2-butyl-1-(2-hydroxypropyl)-1H-imidazole-4-carbonitrile (S7)

$Pd(PPh_3)_2Cl_2$ (0.03 mmol, 0.05 equiv), $K_2CO_3$ (2.1 mmol, 3.5 equiv), 2 (0.6 mmol, 1 equiv), and 3-amino-4-(4,4,5,5-tetramethyl-1,3,2-dioxaborolan-2-yl)phenyl benzenesulfonate (1.4 mmol, 2.3 equiv) was added to a round bottom flask and dissolved in THF (10 mL, 0.06 M) and $H_2O$ (3 mL, 0.2 M). The resulting suspension was heated to 100° C. under $N_2$ until TLC and MS analysis indicated complete conversion. The reaction was then cooled down to 25° C. and concentrated in vacuo. The resulting brown oil was loaded onto a short pad of silica gel, followed by flashing with 40:60-80:20 EtOAc/hex to afford a brown oil that used without further purification in the next step.

e. 4-amino-2-butyl-1-(2-hydroxypropyl)-7-benzenesulphonyl-1H-imidazo[4,5-c]quinoline (S8)

To a round bottom flask containing 5-(2-Amino-4-benzenesulfonyl)-2-butyl-1-(2-hydroxypropyl)-1H-imidazole-4-carbonitrile (0.5 mmol, 1.0 equiv), was added 4N HCl in dioxane (8 mmol, 16 equiv). The reaction was heated at reflux for 4 h then cooled down to 25° C. The reaction was concentrated in vacuo and partitioned between 10% MeOH in EtOAc (50 mL) and saturated $NaHCO_3$ solution (10 mL). The aqueous layer was extracted with 10% MeOH in EtOAc (3×10 mL). The combined organic layers were concentrated in vacuo. The crude residue was purified by silica gel column chromatography afforded the title compound (7% over 2 steps) as a white solid: $R_f$ 0.51 (10:90, MeOH/EtOAc): $^1$H (DMF-d7, 400 MHz) δ 8.30 (d, J=9.0 Hz, 1H), 8.18-8.12 (m, 2H), 8.07-8.00 (m, 1H), 7.95-7.85 (m, 2H), 7.42 (d, J=2.5 Hz, 1H), 7.19 (dd, J=2.5, 9.0 Hz, 1H), 6.85 (2, 2H), 5.45 (d, J=4.9 Hz, 1H), 4.78 (dd, J=3.3, 11.7 Hz, 1H), 4.57 (dd, J=9.2, 15.1 Hz, 1H), 4.43-4.32 (m, 1H), 3.26-3.14 (m, 2H), 2.09 (p, J=7.4 Hz, 2H), 1.67 (sextet, J=7.4 Hz, 2H), 1.52 (d, J=6.3 Hz, 3H), 1.15 (t, J=7.4 Hz, 3H); $^{13}$C (DMF-d7, 100 MHz) δ 155.2, 153.4, 148.0, 146.3, 135.7, 135.1, 133.0, 130.1, 128.7, 122.3, 118.9, 115.3, 114.8, 66.2, 52.7, 29.7, 27.2, 22.6, 20.7, 13.8; HRMS (APCI+): calcd $C_{23}H_{27}N_4O_4S$ $[M+H]^+$ 455.1748. found 455.1754 (error 1.35 ppm).

f. *4-Iodo-3-nitrophenylbenzenesulfonate

To a vial containing 4-iodo-3-nitrophenol (1.03 g, 3.8 mmol, 1 equiv) in $CH_2Cl_2$ (8 mL) was added sequentially benzenesulphonyl chloride (0.73 mL, 5.7 mmol, 1.5 equiv), pyridine (0.9 mL, 11.4 mmol, 3 mmol), and the reaction was stirred for 16 hrs. After which the reaction was diluted with $H_2O$ (10 mL) and extracted with $CH_2Cl_2$ (2×10 mL). The combined organic layers were concentrated in vacuo and purified by column chromatography to afford the title compound as a yellow solid in 98% yield: $R_f$ 0.47 (40:60, EtOAc/hex); $^1$H ($CDCl_3$, 400 MHz) δ 8.00 (d, J=8.6 Hz, 1H), 7.88 (d, J=8.0 Hz, 2H), 7.80-7.70 (m, 1H), 7.64-7.56

(m, 2H), 7.47 (d, J=2.4 Hz, 1H); $^{13}$C (CDCl$_3$, 100 MHz) δ 149.5, 142.9, 135.0, 134.4, 129.6, 128.5, 127.7, 119.9, 105.0, 84.1.

The biological activity of a compound of the invention can be evaluated using the following assays.

Example 3

TLR7/8-NF-κB Reporter Assay:

Human embryonic kidney (HEK) cells that were stably transfected with human TLR-7 or TLR-8 and an NF-κB-responsive secreted embryonic alkaline phosphatase (SEAP) gene (HEK-TLR-7 and -8) were purchased from InvivoGen (San Diego, Calif.). HEK-TLR7/8 cells were stimulated with 30 μM of compound in a 96-well plate in DMEM containing 10% FBS and 0.01% Normocin (InvivoGen) for 24 h. 20 μL of the supernatant from each well was incubated with Quanti-blue substrate solution (InvivoGen) at 37° C. for 1 h and absorbance was read at 650 nm using a Synergy plate reader (Biotek, Winooski, Vt.).

Measurement of Proimflammatory Cytokines with Cytometric Bead Assay:

Bone marrow derived dendritic cells (BMDC) are generated by isolating a single cell suspension of marrow from the femur of C57BL/6 mice (6-8 weeks of age). Red blood cells are lysed with 0.83% NH$_4$Cl, 0.1% KHCO$_3$ and 0.009% 0.5 million cells are seeded in each of well of a 6 well plate in complete RPMI media (Invitrogen, Grand Island, N.Y.), supplemented with mouse 20 ng/ml Granulocyte-Macrophage Colony Stimulating Factor (PeproTech, Rocky Hill, N.J.). After 6 days after culture, BMDC are stimulated with 30 μM of compound for 3 days. 25 μL of supernatant is then removed and assayed for TNFα, IL-12p40, IL-1β and IL-10 using a flow cytometric bead array according to the manufacturers' instructions (BD Bioscience, San Jose, Calif.). Controls are performed using the addition of media and carrier with no drug. Flow cytometry is performed on a FACS canto-II (BD Bioscience) and data are analyzed using Flowjo software (Tree Star, Inc. Ashland, Oreg.).

Data for representative compounds of Formula (I) from the assay of Example 3 is provided in the following Table.

| Compound | TLR-7 EC50[a] (μm) | TLR-8 EC50[a] (μm) |
| --- | --- | --- |
| 539 | 2.35 | N/A[c] |
| 544 | 0.42 | 0.24 |
| 546 | N/A | N/A |
| 548 | 1.53 | 0.29 |
| 549 | 24.6 | 20.6 |
| 556 | 189.4 | N/A |
| 557 | N/A | N/A |
| 558 | 0.18 | 5.34 |
| 563 | 2.9 | N/A |
| 564 | 3.8 | N/A |
| 565 | 6.7 | N/A |
| 566 | 3.3 | N/A |
| 567 | 3.6 | N/A |
| 568 | 4.5 | N/A |
| 569 | 1.74 | N/A |
| 570 | 2.9 | N/A |
| 571 | N/A | 154 |
| 572 | N/A | 66 |
| 573 | N/A | 3.85 |
| 574 | 0.6 | 2.2 |
| 575 | N/A | N/A |
| 576 | N/A | N/A |

[a]HEK SEAP Reporter Assay.
[c]N/A = no activity

Example 4. Evaluation of the Effects on Human Monocyte-Derived Dendritic Cells Materials and Methods 1. Dendritic cells are generated from peripheral blood monocytes as described (Brossart P, et al. Blood. 1998; 92: 4238-4247). In brief, CD14 positive monocytes are from a healthy human peripheral blood mononuclear cells (PBMC) obtained via isolation with Lymphocyte Separation Medium (Mediatech, Inc, Manassas, Va.) and after purification with CD14 microbeads from Miltenyi Biotec Inc (Aubun, Calif.). The CD14 positive monocytes (>95% CD14) are cultured into immature monocyte-derived dendritic cells (MoDC) by further 6 day culture with GM-CSF (100 ng/ml) and IL-4 (100 ng/ml) (R&D, MN).

2. 0.1 million of MoDC are plated into 96-well plate and stimulated for 48 hours with 5 different concentration of following TLRs: 412, 420, 421, 414 and 415 at concentration of 0, 0.325, 1.3, 5.2 and 20.8 nmol/ml in triplicate.

Immunostaining and Flowcytometric Analysis:

48 hours after stimulation, the cells are stained with anti-HLA-DR, CD11c, CD-86, CD80, CD83, CD8a, CD123 and relevant isotype control (eBioscience, San Diego, Calif.). The cells are loaded on FACS-canto II and analyzed with FACSDiva and Flowjo Cytometric Bead Assay (CBA):

The supernatant are harvested 48 hours after stimulation with TLRs. Inflammatory cytokines level is identified with CBA, following the producer's instruction (BD, San Jose, Calif.)

Example 5. Evaluation of IL-6 Level after Stimulation with Compounds of the Invention Material and Method TLR7 mutant mice and C57BL/6j mice, 8-12 weeks old, are obtained from Jackson Lab (Bar Harbor, Me.). TLR7 mutant gene is introduced to 129S1/Sv derived from CJ7 embryonic stem cells. The cell line is backcrossed ten times to C57BL/6Ncr. No TLR7 RNA expression is detected in bone marrow-derived macrophages. The homologues TLR7 mutant mice are developed from backcrossing heterologous mutant mice with wild type C57BL/6j in our Lab. All animals are housed under specific pathogen-free condition and cared for in accordance with the guidelines of University of Minnesota Resource Animal Research.

Single cell suspension of splenocytes from C57BL/6j or TLR7 mutant mice is isolated after whole spleen was squeezed through 70 um cell strainer and red blood cell lysis process. Splenocytes are pulsed in triplicate with 2.08 nmol/ml or 20.8 nmol/ml of Imiquimod (IMQ), hydroxyl Imiquimod (IMQ-OH) or 10 ug/ml of CpG685 in complete RPMI-1640 medium (10% heat-inactivated FBS, glutamine, 1% penicillin/streptomycin, 55 nmol 2-ME, 10 mmol HEPES). Supernatant from the culture medium is harvested 12 hours and 24 hours after pulsing and frozen at −80° C. until detection. A cytometric bead array (BD Biosciences, San Jose, Calif.) are used for measurement of IL-6 level according to the manufacture's instruction. An analysis is performed on FACScanto-II machine with FACSAria II software and further analyzed with Flowjo software (Tree Star, Inc, Ashland, Oreg.). Standard curves and negative control (PBS) are included for calculation of the cytokine concentration in the samples.

Screening Binding Ability of Various Compounds of the Invention to TLR7/8 Cells In Vitro A TLR7 or TLR8 positive cell lines, HEK-Blue TLR cells (Invivogen, San Diego, Calif.), are used for this screening assay. HEK-Blue TLR cells are engineered HEK293 cells. They stably express TLR gene and an inducible NF-kB-SEAP (secreted embryonic alkaline phosphase) report gene. Bounding of ligands with TLR in HEK-Blue cells induces SEAP that has pNPP substrate of phosphase becoming blue. Screening assays are conducted following the manufacture's instruction. TLR ligand compounds, at 20.8 nmol/ml or 5.2 nmol/ml concentration, are added in triplicate in HEK-Blue-TLR7 or TLR8 cells, cultured at 37° C. and 5% $CO_2$ condition. 24 hours later, 5 ul of supernatant of cultures is mixed with 200 ul of pNPP-included detection medium. After one hour SEAP activity is read out as OD at 650 nm with a microplate reader (BioTek Synergy 2, Vermont). No compound solvent (PBS+<1% DMSO) negative control is included.

Inflammatory Cytokine Detection in BMDC and Splenocytes

Bone marrow cells are harvested from femurs and tibias of C57BL/6j. After red blood cells are removed with ammonium-chloride-potassium buffer, the bone marrow cells are cultured with complete RPMI-1640 medium and 2 ng/ml of granulocyte macrophage colony-stimulating factor (GM-CFS) at 5% $CO_2$ and 37° C. for 6 days. Medium is changed twice during 6 days culture. Single cell suspension of splenocytes is prepared in the same way as one in IL-6 detection assay. BMDC or splenocytes are stimulated in triplicate with test compound at various concentration of 20.8 nmol/ml, 5.2 nmol/ml, 1.3 nmol/ml, 0.325 nmol/ml and 0 nmol/ml. 48 hours after stimulation, the supernatants are harvested and frozen at −80° C. until detection. A cytometric bead array (CBA, BD Bioscience) is performed on inflammatory cytokines following the manufacture's instruction. 500 events are collected. Analysis of all samples is performed on FACScanto-II machine with software and further analyzed with Flowjo. Standard curves and negative control (PBS) are included for each cytokine to calculate the cytokine concentration in the samples.

Detection of Co-Stimulator Level on BMDC

Two days after stimulation with compounds, the BMDC are stained in triplicate with different fluorocore-labeled antibodies obtained from eBioscience (San Diego, Calif.). The antibodies include anti-MHC-II (I-A/I-E, clone M5/114.15.2), anti-CD86 (clone GL1), anti-CD80 (clone 16-10A1), anti-CD8α (clone 53-6.7), anti-CD11b (clone, M1/70), antiCD-205 (clone 205yekta), anti-CD3 (clone 17A2) and anti-CD11c (clone N418). All samples are acquired on a FACSCanto II flow cytometer (BD Biosciences, San Jose, Calif.). Between 50,000 and 100,000 events are collected. All data are analyzed with Flowjo software (Tree Star, Inc, Ashland, Oreg.). Gate is based on CD3-CD11c+ population.

Proliferation of Pmel CD8 and IFNγ Production after Cross-Presentation

BMDC from C56BL/6j and single cell suspension of splenocytes from pmel mice (T-cell receptor transgenic mice containing human gp100$_{25-33}$\H2Db specific receptors, Jackson Lab) are prepared as above. BMDC were pulsed in triplicate with 3.5 ug of human gp100 peptide per well (CALLAVGATKVPRNQDWLGVSRQLRTK, GenScript, Piscataway, N.J.) and test compound at the concentration of 10.4 nmol/ml and hgp100 peptide control and PBS negative control for 48 hours. BMDCs were washed twice with complete RPMI medium and followed by coculture with pmel CD8 splenocytes CFSE-labeled that are isolated from pmel splenocytes with CD8+T Cell isolation Kit (Miltenyi Biotec, Auburn, Calif.) at a ratio of 1:3 of DC/CD8. Four days after coculture, supernatants are harvested and frozen at −80° C. until detection of INFγ with CBA kit. CBA for IFNγ measurement is conducted according to manufacture's instruction. The cell pellets are washed and stained with fluorocore-labeled antibodies, all of which are obtained from eBioscience. They are anti-CD3 (clone, 17A2) and anti-CD8α (clone 53-6.7). Flowcytometric data are acquired from the stained samples on FACSCanto II flowcytometer and analyzed with Flowjo software. Gate is from CD3+CD8+ population.

IL-2 Production of OT-I Cells after Stimulation with IMQ-Derived New TLR7 Ligands Single cell suspension of C57BL/6j is prepared as previously. The cells are pulsed in triplicate with test compound at 20.8 nmol/ml concentration and added with and without 15 ug of ovalbumin (Sigma-Aldrich, St. Louis, Mo.) per well. Four days later, the cells are washed twice with complete RPMI medium and cultured with isolated OT-I CD8 T cells using CD8+isolation Kit, (Miltenyi Biotec, Auburn, Calif.). After four days coculture, the supernatant are harvested and detected. CBA is conducted for IL-2 production according to BD Bioscience's instruction. Data are acquired on FACSCanto-II flowcytometer and 500 events are collected and analyzed with Flowjo software.

Example 6. Representative Compounds of the Invention

Using procedures similar to those described herein, the following representative compounds of the invention and salts thereof can be prepared.

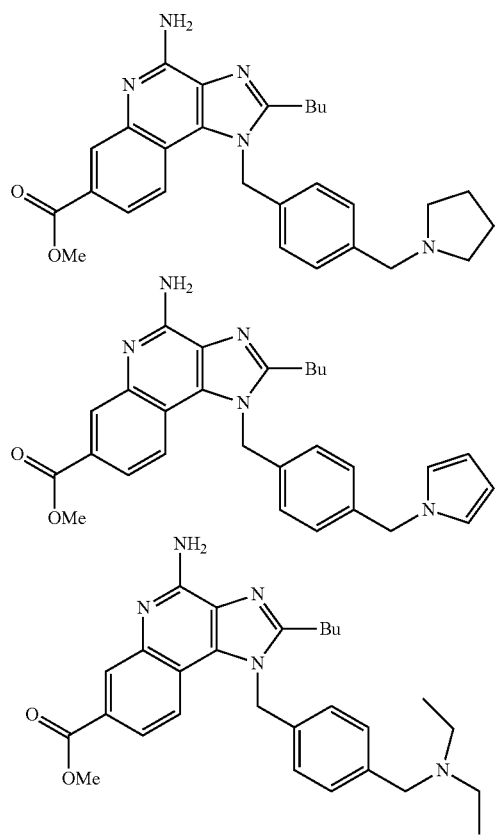

33
-continued
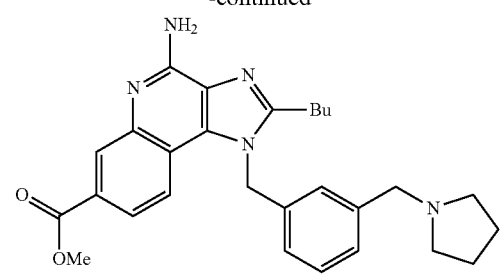
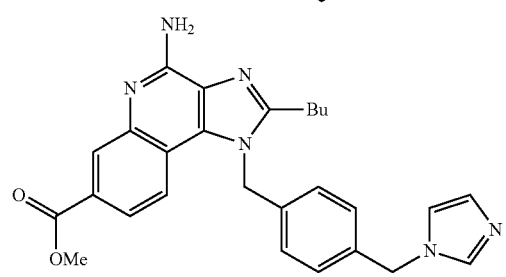
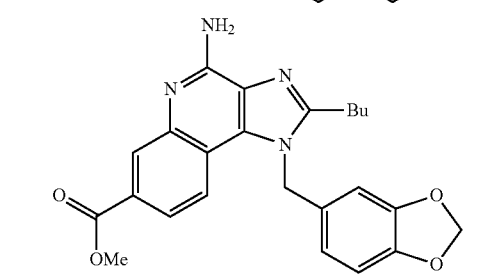
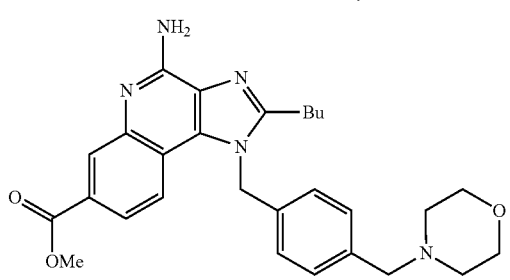
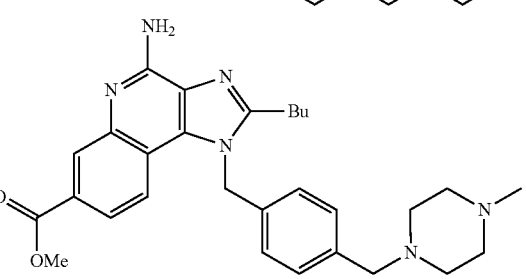
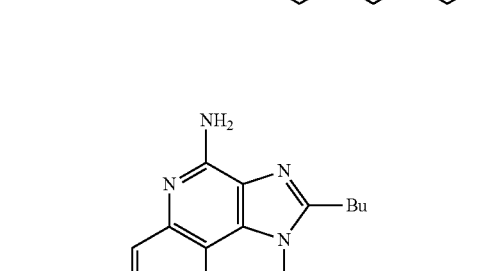
34
-continued
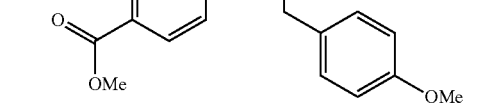

-continued

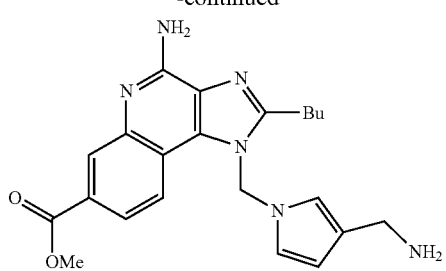
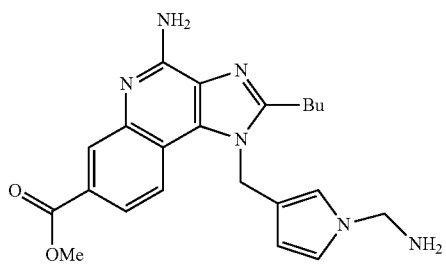
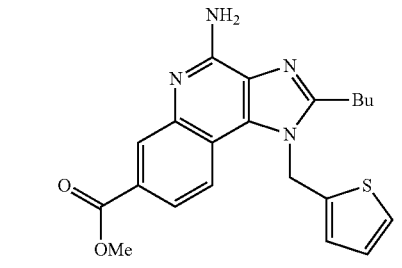
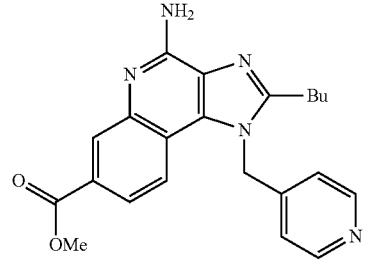
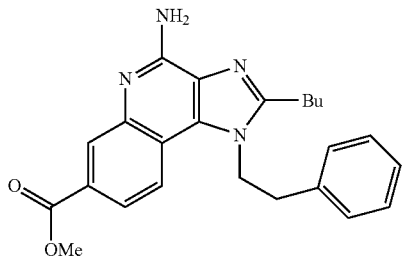
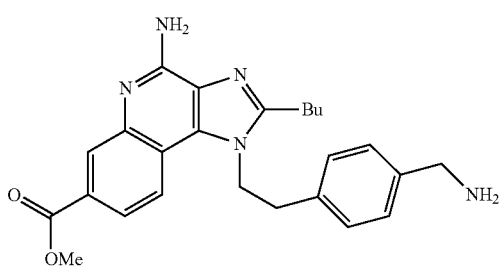

-continued

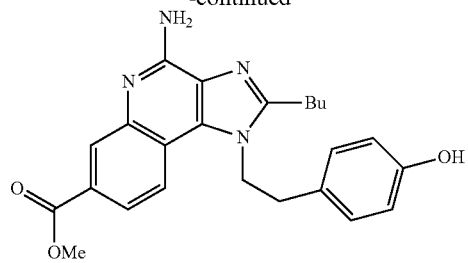

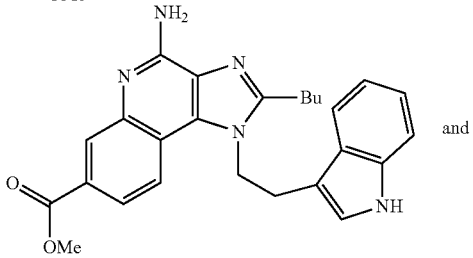

and

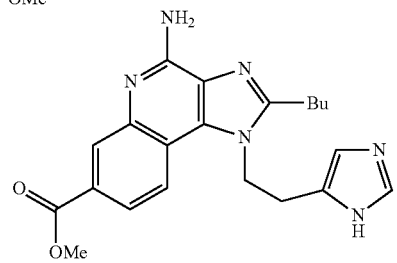

and salts thereof.

Example 7

The following illustrate representative pharmaceutical dosage forms, containing a compound of formula I ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |

| (iii) Capsule | mg/capsule |
|---|---|
| Pregelatinized starch | 120.0 |
| Magnesium stearate | 3.0 |
| | 600.0 |

| (iv) Injection 1 (1 mg/ml) | mg/ml |
|---|---|
| Compound X= (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X= (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

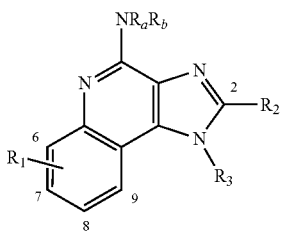

wherein:
R$_1$ is R$^k$—O—C(=O)— or R$^c$R$^d$NC(=O)—;
R$_2$ is H, (C$_1$-C$_6$)alkyl, (C$_2$-C$_6$)alkenyl, (C$_2$-C$_6$)alkynyl, (C$_1$-C$_6$)alkanoyloxy, (C$_3$-C$_6$)cycloalkyl, aryl, heteroaryl, heterocycle, or R$^m$R$^n$NC(=O)—, wherein any (C$_1$-C$_6$)alkyl, (C$_2$-C$_6$)alkenyl, (C$_2$-C$_6$)alkynyl, (C$_1$-C$_6$)alkanoyloxy, (C$_3$-C$_6$)cycloalkyl, aryl, heteroaryl, and heterocycle, is optionally substituted with one or more groups independently selected from the group consisting of hydroxy, halo, —SH, cyano, oxiranyl, (C$_3$-C$_8$)cycloalkyl, aryl, heteroaryl, (C$_1$-C$_6$)alkoxy, (C$_1$-C$_6$)alkylthio, and NR$^g$R$^h$;

R$_3$ is (C$_1$-C$_6$)alkyl that is substituted with one or more groups independently selected from the group consisting of:
halo,
—OR$^z$,
R$^s$C(=O)O—,
aryl that is substituted with (C$_1$-C$_6$)alkyl that is substituted with heteroaryl, NR$^u$R$^v$, or one or more halo,
aryl that is substituted with halo, (C$_1$-C$_6$)alkoxy, —C(=O)NR$^u$R$^v$, or carboxy,
heteroaryl that is optionally substituted with (C$_1$-C$_6$)alkyl that is substituted with heteroaryl, NR$^u$R$^v$, or one or more halo,
heteroaryl that is optionally substituted with halo, (C$_1$-C$_6$)alkoxy, —C(=O)NR$^u$R$^v$, carboxy, (C$_1$-C$_6$)alkoxycarbonyl, and
carboxy;

R$_a$ is H, (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_3$-C$_6$)cycloalkyl, aryl, or heteroaryl, wherein any (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_3$-C$_6$)cycloalkyl, aryl, and heteroaryl is optionally substituted with one or more groups independently selected from hydroxy, halo, —SH, cyano, oxiranyl, (C$_3$-C$_8$)cycloalkyl, aryl, heteroaryl, (C$_1$-C$_6$)alkoxy, (C$_1$-C$_6$)alkylthio, and NR$^g$R$^h$;

R$_b$ is H;

each R$^c$ and R$^d$ is independently H, (C$_1$-C$_6$)alkyl, (C$_2$-C$_6$)alkenyl, (C$_3$-C$_8$)cycloalkyl, (C$_3$-C$_8$)cycloalkyl(C$_1$-C$_6$)alkyl, aryl, or aryl(C$_1$-C$_6$)alkyl; or taken together with the nitrogen to which they are attached form a aziridino, azetidino, morpholino, piperazino, pyrrolidino or piperidino ring, which ring may optionally be substituted with one or more (C$_1$-C$_6$)alkyl;

each R$^g$ and R$^h$ is independently H, (C$_1$-C$_6$)alkyl, (C$_2$-C$_6$)alkenyl, (C$_3$-C$_8$)cycloalkyl, (C$_3$-C$_8$)cycloalkyl(C$_1$-C$_6$)alkyl, aryl, or aryl(C$_1$-C$_6$)alkyl; or taken together with the nitrogen to which they are attached form a aziridino, azetidino, morpholino, piperazino, pyrrolidino or piperidino ring, which ring may optionally be substituted with one or more (C$_1$-C$_6$)alkyl;

R$^k$ is H, (C$_1$-C$_6$)alkyl, (C$_2$-C$_6$)alkenyl, (C$_2$-C$_6$)alkynyl, (C$_3$-C$_8$)cycloalkyl, trifluoromethyl, aryl, or aryl(C$_1$-C$_6$)alkyl, wherein each (C$_1$-C$_6$)alkyl can optionally be substituted with one or more halo, (C$_1$-C$_6$)alkanoyloxy, (C$_1$-C$_6$)alkoxy, or (C$_3$-C$_8$)cycloalkyl;

each R$^m$ and R$^n$ is independently H, (C$_1$-C$_6$)alkyl, (C$_2$-C$_6$)alkenyl, (C$_3$-C$_8$)cycloalkyl, (C$_3$-C$_8$)cycloalkyl(C$_1$-C$_6$)alkyl, aryl, or aryl(C$_1$-C$_6$)alkyl; or taken together with the nitrogen to which they are attached form a aziridino, azetidino, morpholino, piperazino, pyrrolidino or piperidino ring, which ring may optionally be substituted with one or more (C$_1$-C$_6$)alkyl;

wherein the tricyclic ring system in formula (I) can optionally be further substituted on one or more carbons with one or more groups independently selected from the group consisting of halo, hydroxy, nitro, (C$_1$-C$_6$)alkyl, (C$_1$-C$_6$)alkenyl, (C$_1$-C$_6$)alkynyl, (C$_1$-C$_6$)

alkoxy, (C₁-C₆)alkanoyl, (C₁-C₆)alkanoyloxy, (C₁-C₆) alkoxycarbonyl, trifluoromethyl, trifluoromethoxy, cyano, and NR$^p$R$^q$; and each R$^p$ and R$^q$ is independently H or (C₁-C₆)alkyl; or taken together with the nitrogen to which they are attached form a aziridino, azetidino, morpholino, piperazino, pyrrolidino or piperidino ring, which ring may optionally be substituted with one or more (C₁-C₆) alkyl;

R$^s$ is H, aryl, or (C₁-C₁₀)alkyl that is optionally substituted with halo or aryl;

each R$^u$ and R$^v$ is independently H or (C₁-C₆)alkyl; or taken together with the nitrogen to which they are attached form a aziridino, azetidino, morpholino, piperazino, pyrrolidino or piperidino ring, which ring may optionally be substituted with one or more (C₁-C₆) alkyl;

and

R$^z$ is aryl, or (C₁-C₁₀)alkyl that is substituted with halo;

or a salt thereof.

2. The compound of claim 1, wherein R₁ is R$^k$—O—C (=O)—.

3. The compound of claim 1, wherein R₁ is R$^c$R$^d$NC (=O)—.

4. The compound of claim 1, wherein the compound is selected from the group consisting of:

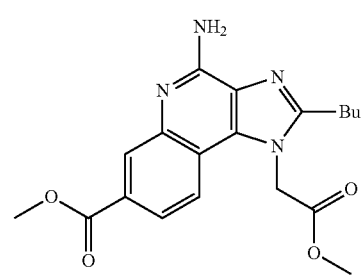

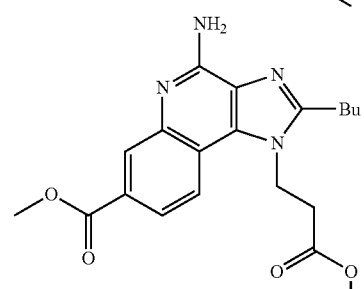

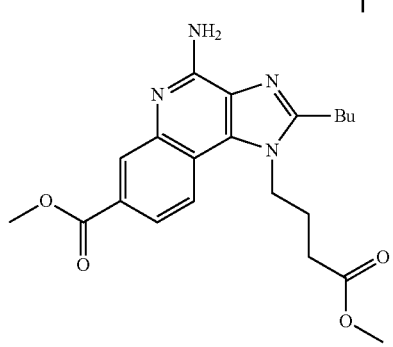

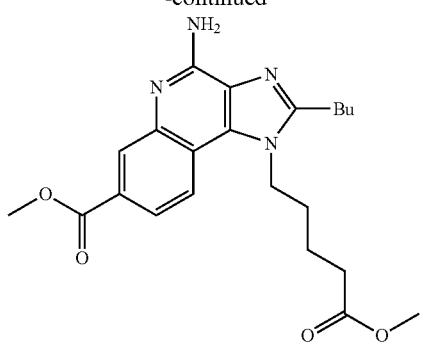

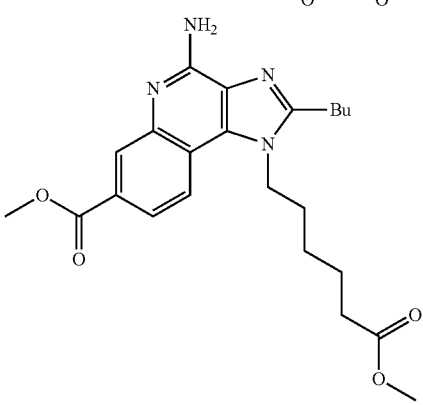

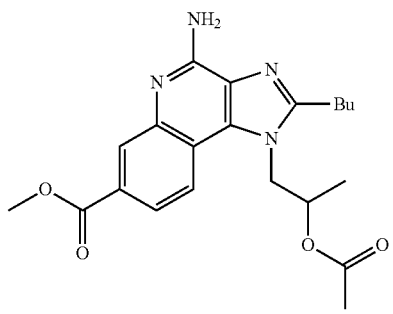

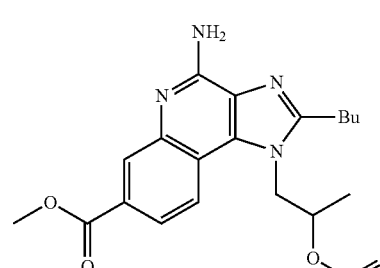

-continued
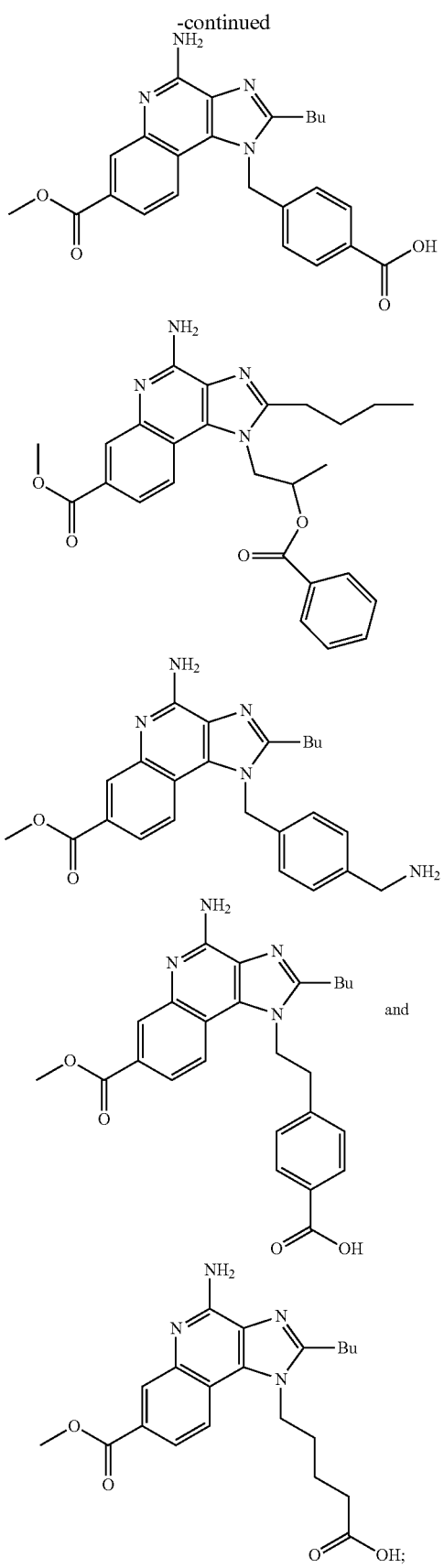
or a pharmaceutically acceptable salt thereof.
5. The compound of claim 1, wherein the compound is selected from the group consisting of:
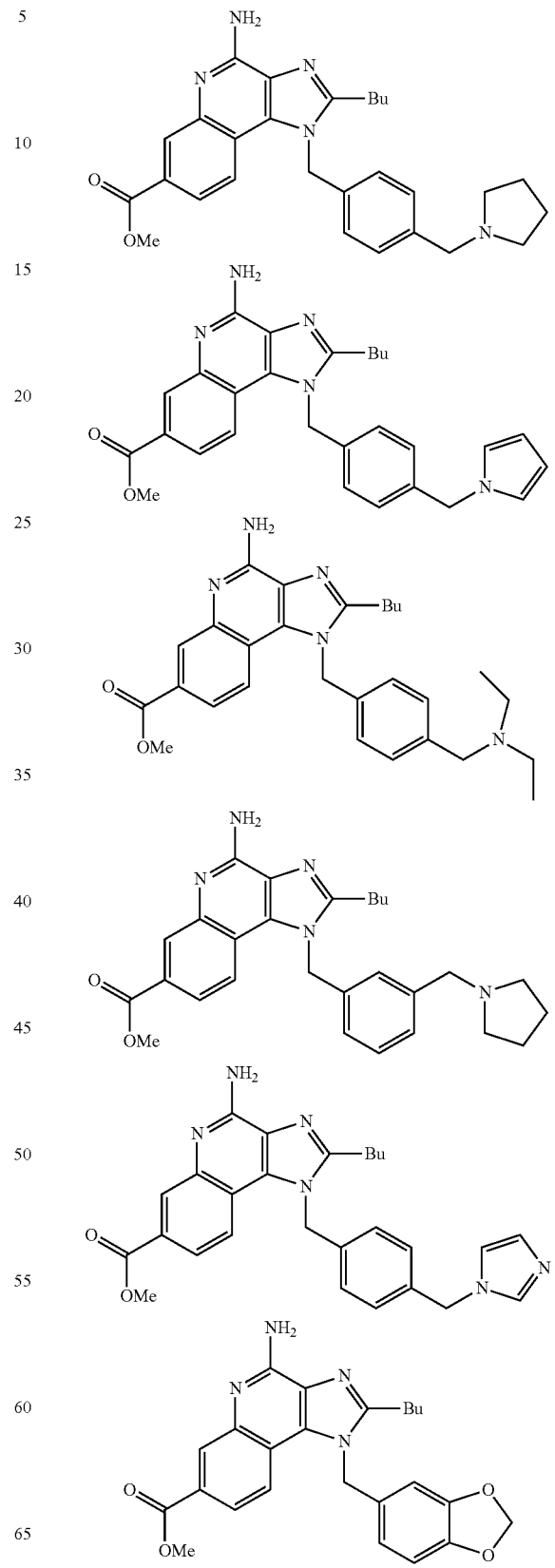
and -continued
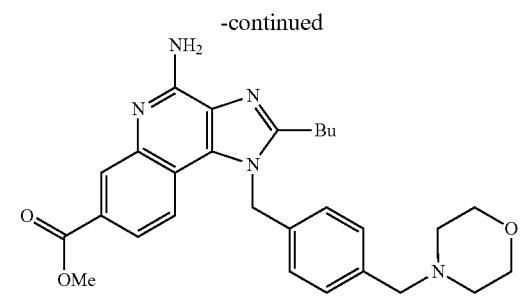
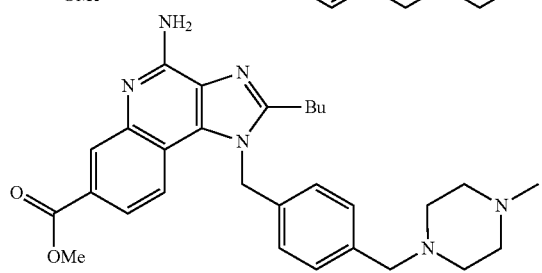
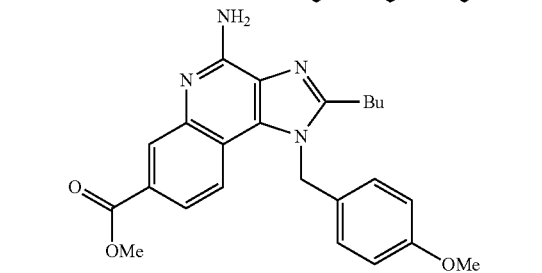
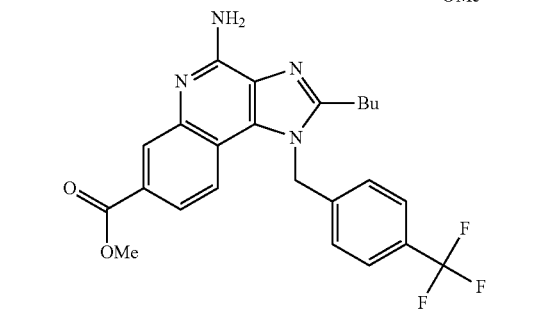
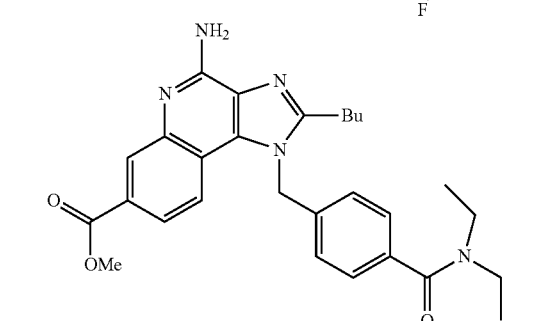
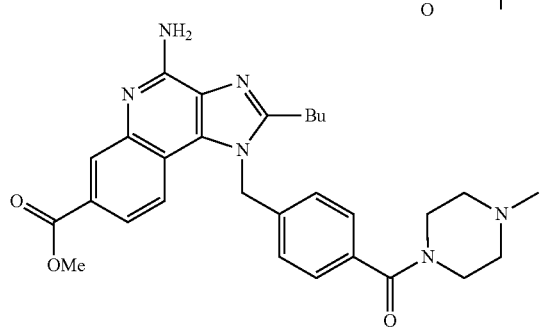
-continued
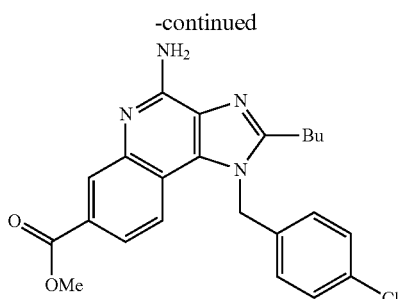
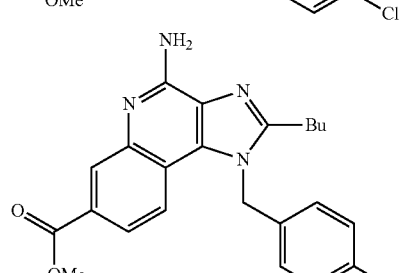
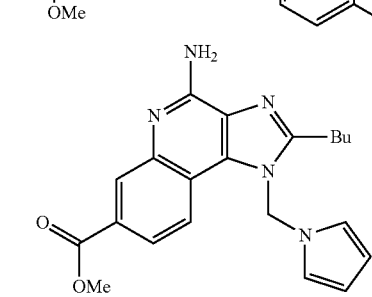
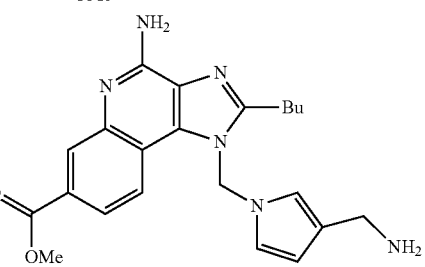
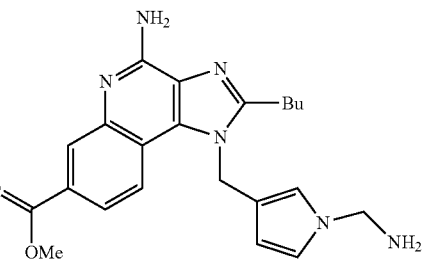
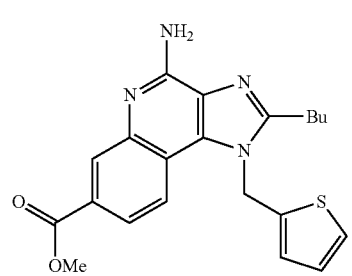

-continued

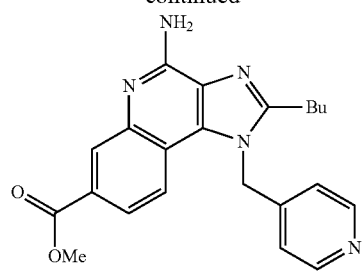

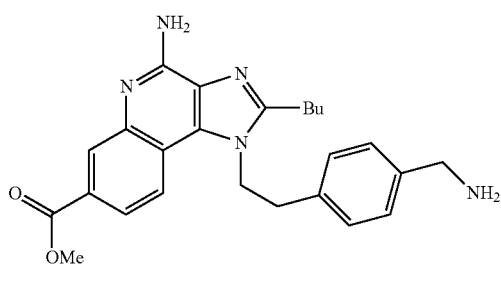

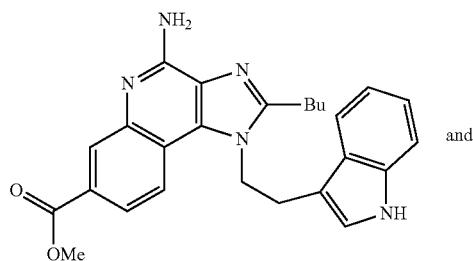 and

-continued

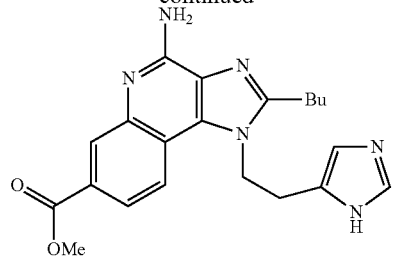

or a pharmaceutically acceptable salt thereof.

6. The compound,

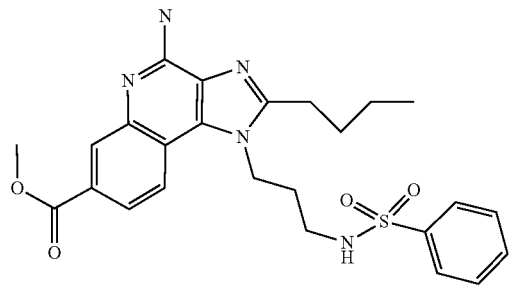 [SMILES: CCCCc1nc2c(N)nc3cc(C(=O)OC)ccc3c2n1CCCNS(=O)(=O)c1ccccc1]

or a pharmaceutically acceptable salt thereof.

7. The compound of claim 1, wherein $R^k$ is $(C_1)$alkyl.
8. The compound of claim 1, wherein $R^k$ is H.
9. The compound of claim 1, wherein the compound is:

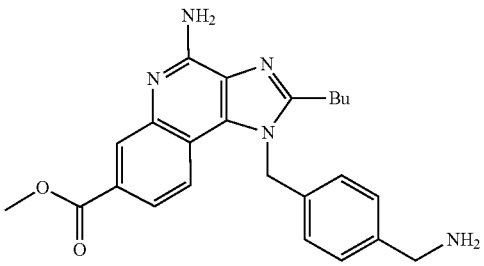

or a pharmaceutically acceptable salt thereof.

10. The compound of claim 1, wherein $R_3$ is —$OR^z$.
11. The compound of claim 1, wherein $R_3$ is $(C_1$-$C_6)$alkyl that is substituted with aryl that is substituted with $(C_1$-$C_6)$ alkyl that is substituted with heteroaryl, $NR^uR^v$, or one or more halo.
12. The compound of claim 1 wherein $R_2$ is $(C_1$-$C_6)$alkyl.

* * * * *